United States Patent
Chen

(10) Patent No.: US 8,801,780 B2
(45) Date of Patent: Aug. 12, 2014

(54) PLUNGER TIP COUPLING DEVICE FOR INTRAOCULAR LENS INJECTOR

(75) Inventor: Bill Chen, Irvine, CA (US)

(73) Assignee: Alcon Research, Ltd., Fort Worth, TX (US)

(*) Notice: Subject to any disclaimer, the term of this patent is extended or adjusted under 35 U.S.C. 154(b) by 322 days.

(21) Appl. No.: 13/069,179

(22) Filed: Mar. 22, 2011

(65) Prior Publication Data
US 2011/0172676 A1     Jul. 14, 2011

Related U.S. Application Data

(63) Continuation-in-part of application No. 12/249,996, filed on Oct. 13, 2008, now Pat. No. 8,308,736.

(51) Int. Cl.
*A61F 9/00*     (2006.01)
*A61F 2/16*     (2006.01)

(52) U.S. Cl.
CPC ............. *A61F 2/1662* (2013.01); *A61F 2/1672* (2013.01)
USPC ........................................ 623/6.12; 606/107

(58) Field of Classification Search
USPC ........................................ 606/107; 623/6.12
See application file for complete search history.

(56) References Cited

U.S. PATENT DOCUMENTS

| | | | |
|---|---|---|---|
| 4,573,998 A | 3/1986 | Mazzocco |
| 4,619,657 A | 10/1986 | Keates et al. |
| 4,681,102 A | 7/1987 | Bartell |
| 4,747,404 A | 5/1988 | Jampel et al. |
| 4,834,094 A | 5/1989 | Patton et al. |
| 4,836,201 A | 6/1989 | Patton et al. |
| 4,919,130 A | 4/1990 | Stoy et al. |
| 4,934,363 A | 6/1990 | Smith et al. |
| 4,960,557 A | 10/1990 | Sorensen |
| 5,007,913 A | 4/1991 | Dulebohn et al. |
| 5,026,396 A | 6/1991 | Darin |

(Continued)

FOREIGN PATENT DOCUMENTS

| | | |
|---|---|---|
| AU | 728443 | 1/2001 |
| DE | 4301573 | 7/1994 |

(Continued)

OTHER PUBLICATIONS

International Search Report for PCT/US2012/030147, Publication No. WO2012/129419, dated Jul. 13, 2010, 2 pages.

(Continued)

*Primary Examiner* — Kathleen Holwerda
*Assistant Examiner* — Sarah W Aleman
(74) *Attorney, Agent, or Firm* — Darien Reddick

(57) ABSTRACT

The present disclosure is directed to devices, systems, and methods directed to mounting a plunger tip to a plunger of an IOL injection device. A plunger tip wrench that is operable to releasably retain a plunger tip may be coupled to a holder extending from an end of the IOL injection device to align the plunger tip with the plunger of the IOL injection device. In some instances, the IOL injection device may include a motor and use a back electromotive force (EMF) of the motor to detect a position of the plunger as it is extended to engage the plunger tip. The plunger tip may be positioned relative to the plunger such that the plunger will engage the plunger tip within the entire range of a negative error position and a positive error position.

4 Claims, 22 Drawing Sheets

(56) References Cited

U.S. PATENT DOCUMENTS

| | | |
|---|---|---|
| 5,098,439 A | 3/1992 | Hill et al. |
| 5,190,552 A | 3/1993 | Kelman |
| 5,275,604 A | 1/1994 | Rheinish et al. |
| 5,304,182 A | 4/1994 | Rheinish et al. |
| 5,354,333 A | 10/1994 | Kammann et al. |
| 5,397,313 A | 3/1995 | Gross |
| 5,425,734 A | 6/1995 | Blake |
| 5,444,183 A | 8/1995 | Gehrs et al. |
| 5,464,396 A | 11/1995 | Barta et al. |
| 5,468,246 A | 11/1995 | Blake |
| 5,494,484 A | 2/1996 | Feingold |
| 5,496,278 A | 3/1996 | Buff |
| 5,496,328 A | 3/1996 | Nakajima et al. |
| 5,499,987 A | 3/1996 | Feingold |
| 5,578,042 A | 11/1996 | Cumming |
| 5,582,614 A | 12/1996 | Feingold |
| 5,607,433 A | 3/1997 | Polla et al. |
| 5,616,148 A | 4/1997 | Eagles et al. |
| 5,620,450 A | 4/1997 | Eagles et al. |
| 5,629,577 A | 5/1997 | Polla et al. |
| 5,643,275 A | 7/1997 | Blake |
| 5,643,276 A | 7/1997 | Zaleski |
| 5,653,715 A | 8/1997 | Reich et al. |
| 5,653,753 A | 8/1997 | Brady et al. |
| 5,716,364 A | 2/1998 | Makker et al. |
| 5,728,102 A | 3/1998 | Feingold et al. |
| 5,735,858 A | 4/1998 | Makker et al. |
| 5,772,666 A | 6/1998 | Feingold et al. |
| 5,776,138 A * | 7/1998 | Vidal et al. .................. 606/107 |
| 5,800,441 A | 9/1998 | Polla et al. |
| 5,800,442 A | 9/1998 | Wolf et al. |
| 5,803,925 A | 9/1998 | Yang et al. |
| 5,810,834 A | 9/1998 | Heyman |
| 5,820,373 A | 10/1998 | Okano et al. |
| 5,860,986 A | 1/1999 | Reich et al. |
| 5,868,752 A | 2/1999 | Makker et al. |
| 5,873,879 A | 2/1999 | Figueroa et al. |
| 5,876,406 A | 3/1999 | Wolf et al. |
| 5,876,407 A | 3/1999 | Makker et al. |
| 5,891,153 A | 4/1999 | Peterson |
| 5,944,725 A | 8/1999 | Cicenas et al. |
| 5,947,976 A | 9/1999 | Van Noy et al. |
| 6,010,510 A | 1/2000 | Brown et al. |
| 6,042,587 A | 3/2000 | Polla et al. |
| 6,056,757 A | 5/2000 | Feingold |
| 6,056,758 A | 5/2000 | Vidal |
| 6,083,231 A | 7/2000 | Van Noy et al. |
| 6,140,602 A | 10/2000 | Costin |
| 6,143,001 A | 11/2000 | Brown et al. |
| 6,162,229 A | 12/2000 | Feingold et al. |
| 6,162,230 A | 12/2000 | Polla et al. |
| 6,163,963 A | 12/2000 | Huang |
| 6,179,843 B1 | 1/2001 | Weiler |
| 6,228,094 B1 | 5/2001 | Erdman |
| 6,254,607 B1 | 7/2001 | Makker et al. |
| 6,276,014 B1 | 8/2001 | Lee |
| 6,334,862 B1 | 1/2002 | Vidal et al. |
| 6,355,046 B2 | 3/2002 | Kikuchi et al. |
| 6,423,035 B1 | 7/2002 | Das et al. |
| 6,447,519 B1 | 9/2002 | Brady et al. |
| 6,471,708 B2 | 10/2002 | Green |
| 6,497,708 B1 | 12/2002 | Cumming |
| 6,500,181 B1 | 12/2002 | Portney |
| 6,503,275 B1 | 1/2003 | Cumming |
| 6,558,395 B2 * | 5/2003 | Hjertman et al. ............ 606/107 |
| 6,592,591 B2 | 7/2003 | Polla et al. |
| 6,607,537 B1 | 8/2003 | Binder |
| 6,635,731 B2 | 10/2003 | Mentak |
| 6,666,871 B2 | 12/2003 | Kikuchi et al. |
| 6,685,740 B2 | 2/2004 | Figueroa et al. |
| 6,887,221 B1 * | 5/2005 | Baillargeon et al. ......... 606/107 |
| 6,899,717 B2 | 5/2005 | Weber et al. |
| 6,923,815 B2 | 8/2005 | Brady et al. |
| 6,964,648 B2 | 11/2005 | Talling et al. |
| 6,976,989 B1 | 12/2005 | Vincent |
| 7,014,641 B2 | 3/2006 | Kobayashi et al. |
| 7,042,180 B2 | 5/2006 | Terry et al. |
| 7,097,649 B2 * | 8/2006 | Meyer ........................... 606/107 |
| 7,131,976 B2 | 11/2006 | Kobayashi et al. |
| 7,156,854 B2 | 1/2007 | Brown et al. |
| 7,156,855 B2 | 1/2007 | Oda |
| 7,189,218 B2 | 3/2007 | Lichtenberg |
| 7,279,006 B2 | 10/2007 | Vincent |
| 7,422,604 B2 | 9/2008 | Vaquero et al. |
| 7,429,263 B2 | 9/2008 | Vaquero et al. |
| 8,109,938 B2 * | 2/2012 | Pessin ........................... 606/107 |
| 2001/0007075 A1 | 7/2001 | Hjertman et al. |
| 2002/0022881 A1 | 2/2002 | Figueroa et al. |
| 2003/0040755 A1 | 2/2003 | Meyer |
| 2003/0135221 A1 | 7/2003 | Sabet |
| 2003/0139749 A1 | 7/2003 | Kikuchi et al. |
| 2003/0212406 A1 | 11/2003 | Kobayashi et al. |
| 2003/0212409 A1 | 11/2003 | Kobayashi et al. |
| 2004/0054374 A1 | 3/2004 | Weber et al. |
| 2004/0059343 A1 | 3/2004 | Shearer et al. |
| 2004/0087896 A1 | 5/2004 | Wise et al. |
| 2004/0097956 A1 | 5/2004 | Oda |
| 2004/0127911 A1 | 7/2004 | Figueroa et al. |
| 2004/0147938 A1 | 7/2004 | Dusek et al. |
| 2004/0160575 A1 | 8/2004 | Ayton et al. |
| 2004/0199174 A1 | 10/2004 | Herberger et al. |
| 2004/0215207 A1 | 10/2004 | Cumming |
| 2004/0238392 A1 | 12/2004 | Peterson et al. |
| 2005/0029976 A1 | 2/2005 | Terry et al. |
| 2005/0049605 A1 | 3/2005 | Vaquero et al. |
| 2005/0049606 A1 | 3/2005 | Vaquero et al. |
| 2005/0065534 A1 | 3/2005 | Hohl |
| 2005/0143750 A1 | 6/2005 | Vaquero |
| 2005/0149056 A1 | 7/2005 | Rathert |
| 2005/0149057 A1 | 7/2005 | Rathert |
| 2005/0203619 A1 | 9/2005 | Altmann |
| 2005/0222578 A1 | 10/2005 | Vaquero |
| 2005/0222579 A1 | 10/2005 | Vaquero et al. |
| 2006/0066962 A1 | 3/2006 | Totzeck et al. |
| 2006/0085013 A1 | 4/2006 | Dusek et al. |
| 2006/0167466 A1 | 7/2006 | Dusek |
| 2006/0184181 A1 | 8/2006 | Cole et al. |
| 2006/0200167 A1 | 9/2006 | Peterson et al. |
| 2006/0229633 A1 | 10/2006 | Shepherd |
| 2006/0229634 A1 | 10/2006 | Shepherd |
| 2006/0235429 A1 | 10/2006 | Lee et al. |
| 2006/0284581 A1 | 12/2006 | Mullin et al. |
| 2007/0005135 A1 | 1/2007 | Makker et al. |
| 2007/0050023 A1 | 3/2007 | Bessiere et al. |
| 2007/0060925 A1 | 3/2007 | Pynson |
| 2007/0150056 A1 | 6/2007 | Meyer |
| 2007/0173860 A1 | 7/2007 | Iwaski |
| 2008/0033449 A1 | 2/2008 | Cole et al. |
| 2008/0039862 A1 | 2/2008 | Tran |
| 2008/0058830 A1 | 3/2008 | Cole et al. |
| 2008/0097459 A1 | 4/2008 | Kammerlander et al. |
| 2008/0119865 A1 | 5/2008 | Meunier et al. |
| 2008/0200920 A1 | 8/2008 | Downer |
| 2008/0200921 A1 | 8/2008 | Downer |
| 2008/0221584 A1 | 9/2008 | Downer |
| 2008/0221585 A1 | 9/2008 | Downer |
| 2008/0255577 A1 | 10/2008 | Downer |
| 2009/0043313 A1 | 2/2009 | Ichinohe et al. |
| 2009/0112223 A1 | 4/2009 | Downer |
| 2009/0171366 A1 | 7/2009 | Tanaka |
| 2009/0204123 A1 | 8/2009 | Downer |
| 2009/0216244 A1 | 8/2009 | Pynson |
| 2010/0094309 A1 | 4/2010 | Boukhny et al. |
| 2010/0121340 A1 | 5/2010 | Downer |

FOREIGN PATENT DOCUMENTS

| | | |
|---|---|---|
| EP | 0174917 | 3/1986 |
| EP | 0 270 257 | 6/1988 |
| EP | 0 363 213 | 4/1990 |
| EP | 0477466 | 6/1996 |
| EP | 0820211 | 1/1998 |
| EP | 0 858 304 | 8/1998 |
| EP | 0962195 | 12/1999 |

(56) References Cited

FOREIGN PATENT DOCUMENTS

| | | |
|---|---|---|
| EP | 1 011 561 | 6/2000 |
| EP | 1 076 408 | 2/2001 |
| EP | 1 332 731 A1 | 8/2003 |
| EP | 1 332 731 B1 | 8/2003 |
| EP | 1360944 | 11/2003 |
| EP | 1481652 | 12/2004 |
| EP | 1661533 | 5/2006 |
| EP | 1832247 | 9/2007 |
| EP | 1849436 A1 | 10/2007 |
| EP | 1891911 | 2/2008 |
| EP | 1958593 | 8/2008 |
| EP | 2062552 | 5/2009 |
| FR | 2820633 | 8/2002 |
| GB | 2 224 214 | 5/1990 |
| JP | 1176288 | 12/1989 |
| JP | H09-506285 | 2/1996 |
| JP | 10309294 | 11/1998 |
| JP | 10511876 | 11/1998 |
| JP | 10512460 | 11/1998 |
| JP | 2000025073 | 1/2000 |
| JP | 2000513955 | 10/2000 |
| JP | 2003048488 | 2/2003 |
| JP | 2003070829 | 3/2003 |
| JP | 2003325569 | 11/2003 |
| JP | 2006006817 | 1/2006 |
| JP | 2006014962 | 1/2006 |
| JP | 2006181269 | 7/2006 |
| JP | 2007055057 | 3/2007 |
| JP | 2007-215990 | 8/2007 |
| RU | 2138232 | 9/1999 |
| RU | 2171100 | 7/2001 |
| RU | 2238283 | 10/2004 |
| RU | 2242956 | 12/2004 |
| SU | 1440496 | 11/1988 |
| WO | WO 9407436 A1 | 4/1994 |
| WO | WO 94/20027 | 9/1994 |
| WO | WO 96/10372 | 4/1996 |
| WO | WO 96/20662 | 7/1996 |
| WO | WO 96/28122 | 9/1996 |
| WO | 9629956 | 10/1996 |
| WO | WO 96/29956 | 10/1996 |
| WO | WO 97/15253 | 5/1997 |
| WO | WO 97/26841 | 7/1997 |
| WO | WO 98/05281 | 2/1998 |
| WO | WO 98/12969 | 4/1998 |
| WO | WO 98/15244 | 4/1998 |
| WO | WO 98/20819 | 5/1998 |
| WO | WO 00/40175 | 7/2000 |
| WO | WO 00/62712 | 10/2000 |
| WO | WO 2004/091447 | 10/2004 |
| WO | WO 2005/018515 | 3/2005 |
| WO | WO 2005/020853 | 3/2005 |
| WO | WO 2005/023154 A2 | 3/2005 |
| WO | WO 2005/023154 A3 | 3/2005 |
| WO | WO 2005/102223 | 11/2005 |
| WO | WO 2006/059183 | 6/2006 |
| WO | 2006-070628 | 7/2006 |
| WO | WO 2006/070561 | 7/2006 |
| WO | WO 2006/080191 | 8/2006 |
| WO | WO 2006/113138 | 10/2006 |
| WO | WO 2006/113357 | 10/2006 |
| WO | WO 2007/054645 * | 5/2007 ................ 606/107 |

OTHER PUBLICATIONS

International Search Report for PCT/US2009/057,083, Filed Sep. 16, 2009, Publication No. WO2010/044,974, Published Apr. 22, 2010, dated Dec. 30, 2009, 5 pages.
Abstract of article entitled "Implantation of the AcrySof MA30BA lens using the Monarch System" by Barakova D., original article found in Cesk slov Oftalmol, May 2002 58(3), at p. 149-152, found in PubMed database at http://www.ncbi.nlm.nih.gov/pubmed/12087658 (1 page).
European Search Report for Application No. 08102172.7, Publication No. 1980219, dated Oct. 15, 2008, 5 pages.
International Search Report for PCT/US2011/032708, Publication No. W02011/133427, dated Jun. 29, 2011, 2 pages.
Written Opinion of the International Searching Authority, International Application No. PCT/US2011/032708, dated Jun. 29, 2011, 4 pages.
International Search Report for PCT/US2010/023544, Publication No. WO2010/093593, dated May 28, 2010, 4 pages.
PCT International Preliminary Report on Patentability and Written Opinion, PCT/US2010/023544, dated Aug. 16, 2011, 4 pages.
International Preliminary Report on Patentability, PCT/US2009/057083, dated Apr. 19, 2011, 7 pages.
European Search Report for Application No. 07114085.9, Publication No. EP1891911, dated Jan. 14, 2008, 2 pages.
European Search Report for Application No. 08100876.5, Publication No. EP1958593, dated Apr. 22, 2008, 2 pages.
European Search Report for Application No. 09154535.0, Publication No. EP2062552, dated Apr. 15, 2009, 2 pages.
PCT International Preliminary Report on Patentability and Written Opinion, PCT/US2012/030147, filed Mar. 22, 2012, Publication No. 2012/129,419, Published Sep. 27, 2012, dated Sep. 24, 2013, 9 pages.
Extended European Search Report for Application No. 11772480.7, Publication No. EP2528561, dated Oct. 2, 2013, 5 pages.
Shao; "Direct Back EMF Detection Method for Sensorless Brushless DC (BLDC) Motor Drives"; Virginia Polytechnic Institute and State University, Blacksburg, Virginia; Sep. 2003 (http://scholar.lib.vt.edu/theses/available/etd-09152003-171904/unrestricted/T.pdf); 91 pages.

* cited by examiner

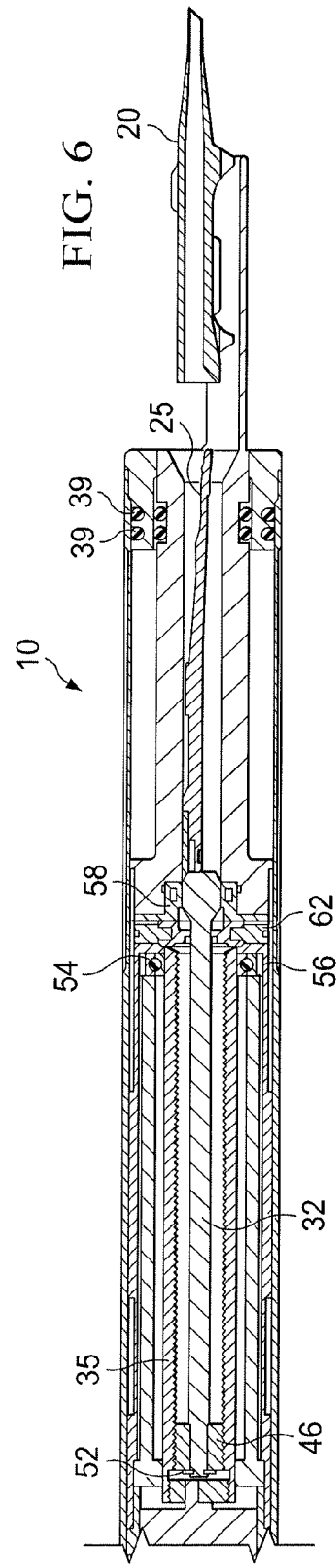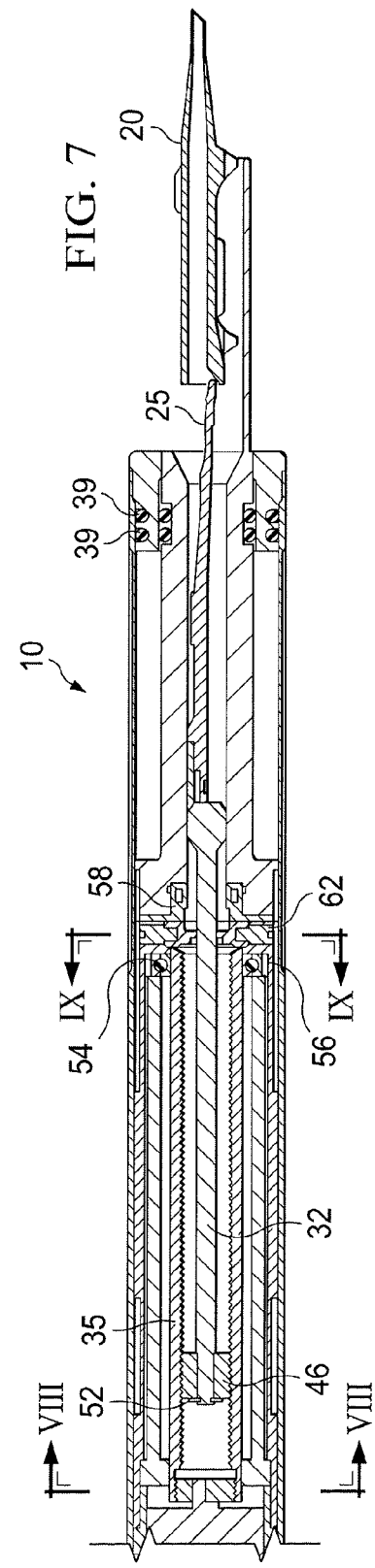

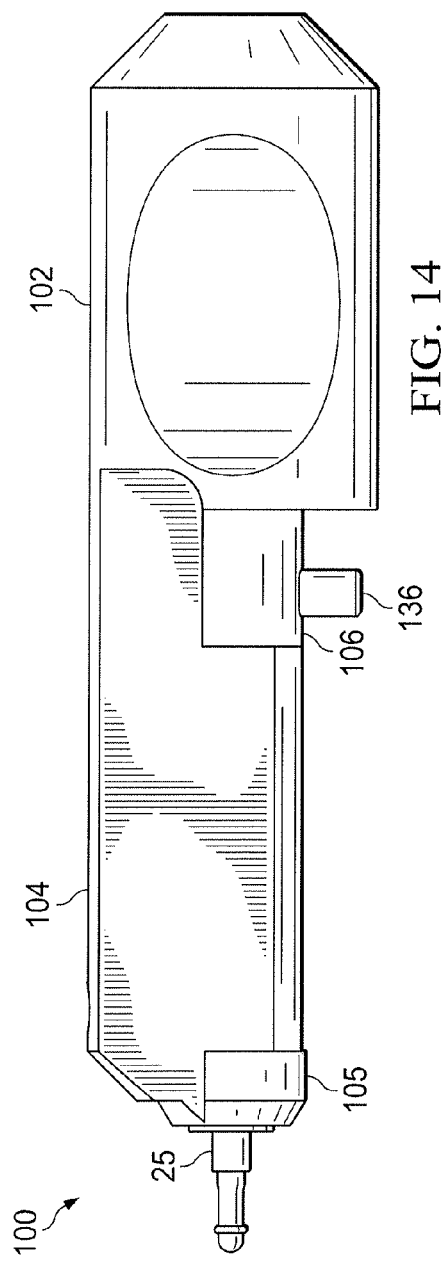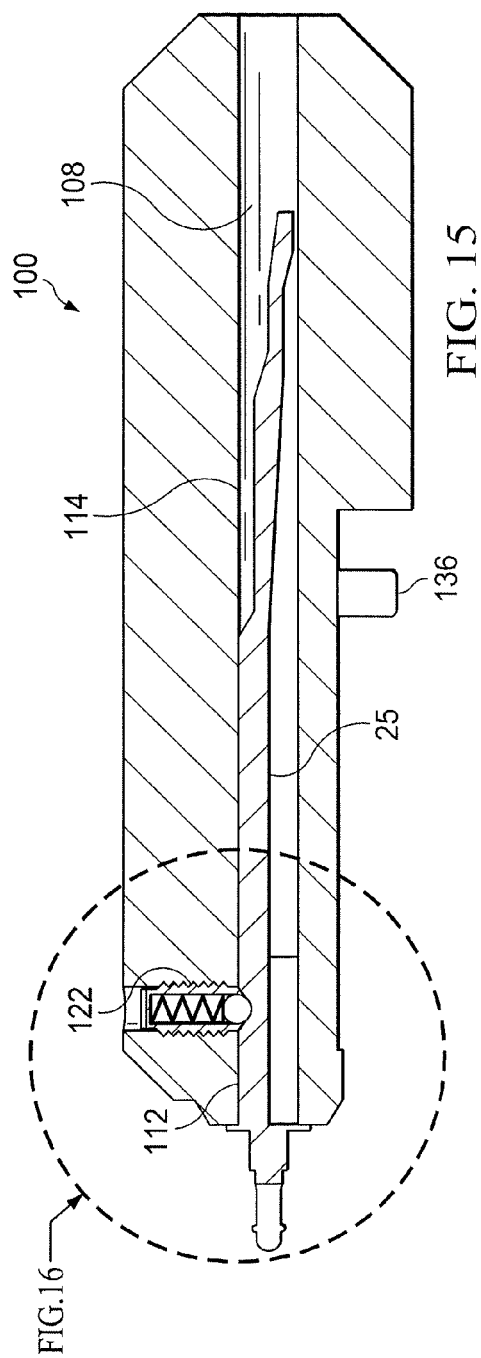

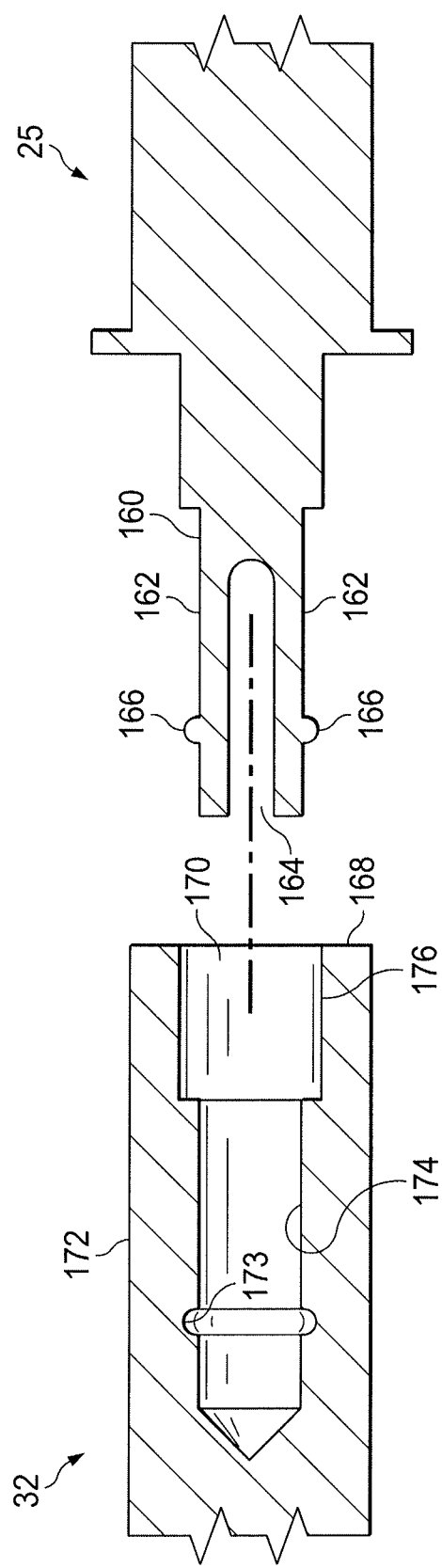

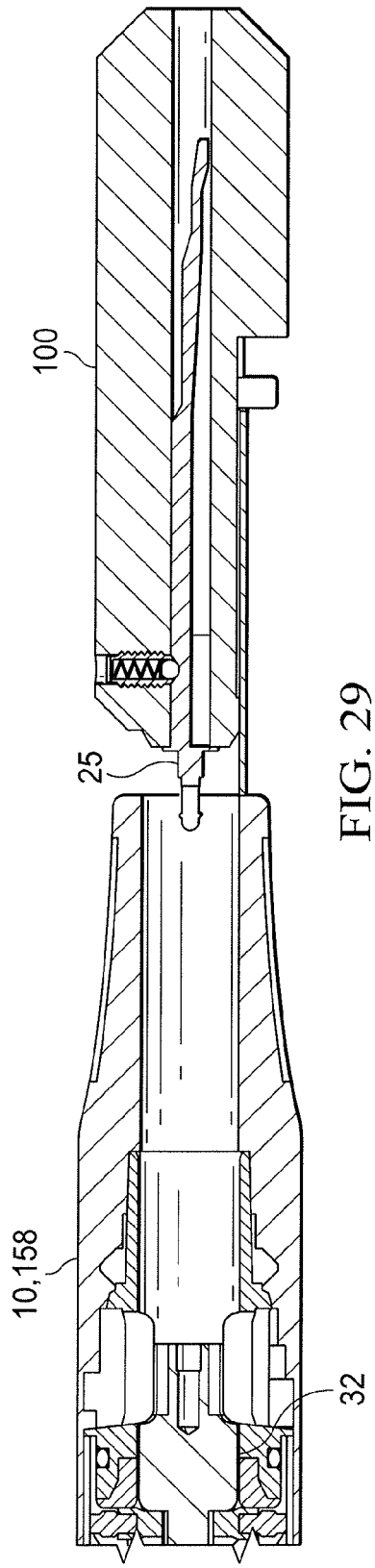
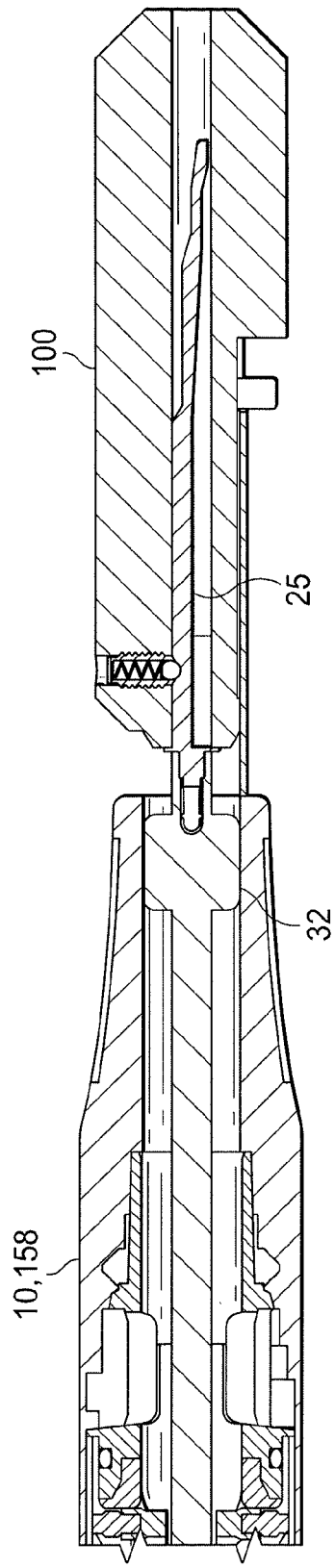

PLUNGER TIP COUPLING DEVICE FOR INTRAOCULAR LENS INJECTOR

CROSS-REFERENCE TO RELATED APPLICATIONS

This application is a continuation-in-part of prior application Ser. No. 12/249,996, filed Oct. 13, 2008 now U.S. Pat. No. 8,308,736, the entirety of which is incorporated herein by reference.

TECHNICAL FIELD

The present disclosure relates generally to a device for delivering an intraocular lens into an eye and more particularly to fault detection in such a device.

BACKGROUND

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, an opening is made in the anterior capsule and a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

The IOL is injected into the eye through the same small incision used to remove the diseased lens. An insertion cartridge of an IOL injector is loaded with the IOL, the tip of the insertion cartridge is inserted into the incision, and the lens is delivered into the eye.

Many IOLs manufactured today are made from a polymer with specific characteristics. These characteristics allow the lens to be folded, and when delivered into the eye, allow the lens to unfold into the proper shape. Several manual injector devices are available for implanting these lenses into the eye. However, threaded-type manual injectors require the use of two hands, which is cumbersome and tedious. Syringe-type injectors produce inconsistent injection force and displacement. Thus, improved devices and methods are needed for delivering IOLs into the eye.

SUMMARY

According to one aspect, the disclosure describes a plunger tip wrench including a body defining a first bore adapted to receive a plunger tip; a first alignment feature defined on an exterior surface of the body, the first alignment feature adapted to align the plunger tip wrench at a desired position; a second alignment feature extending from the exterior surface of the body, the second alignment feature comprising a member extending radially outwardly from the body; and a detent mechanism in communication with the first bore. The detent mechanism may be adapted to releasably retain the plunger tip within the first bore. The first bore may include a first bore portion and a second bore portion. The first bore portion may include an orientation-defining structure adapted to orient the plunger tip within the first bore at a defined orientation.

Another aspect of the disclosure encompasses a system for inserting an intraocular lens (IOL) into an eye. The system may include an IOL injection device, a plunger tip wrench, and a plunger tip. The IOL injection device may include a housing defining a first longitudinal bore having a longitudinal axis, a plunger displaceable within the longitudinal bore, and a cartridge holder extending from an end of the housing. The cartridge holder may include tabs formed on opposing sides of the cartridge holder and a slot formed in a leading edge of the cartridge holder. The plunger tip wrench may be insertable into the cartridge holder.

The plunger tip wrench may include a body defining a second longitudinal bore including a first bore portion and a second bore portion, a first alignment feature defined on an exterior surface of the body such that the first alignment feature and the tabs of the cartridge holder cooperate to align the first longitudinal bore with the second longitudinal bore, and a second alignment feature extending outwardly from the body. The second alignment feature may be received within the slot formed in the leading edge of the cartridge holder such that the second alignment feature and the slot cooperate to radially align the plunger tip wrench relative to the IOL injection device. The plunger tip wrench may also include a detent mechanism in communication with the second longitudinal bore. The plunger tip may be received within the second longitudinal bore and releasably retained therein by the detent mechanism. Also, the plunger tip may be adapted to be releasably coupled to the plunger of the IOL injection device.

Another aspect may include a method of coupling a plunger tip to a plunger of an IOL injection device. The method may include locating a plunger tip in alignment with the plunger, extending the plunger from an initial position towards the plunger tip to an engagement position, coupling the plunger and the plunger tip together, and retracting the plunger and plunger tip to the initial position.

The various aspects may include one or more of the following features. The orientation-defining structure of the first bore portion may include a planar surface adapted to cooperate with a corresponding planar surface of the plunger tip. The body of a plunger tip wrench may include a grip portion comprising recesses formed therein and an elongate portion. The first bore may extend through both the grip portion and the elongate portion. The first alignment feature may include at least one enlarged portion extending outwardly from the body. The at least one enlarged portion may include a first enlarged portion disposed at an end of the elongate portion and a second enlarged portion disposed on the elongate portion adjacent the grip portion. The first alignment feature may include at least one enlarged portion extending outwardly from the body. The second alignment feature may include a pair of protrusions laterally offset from each other. The pair of protrusions may be laterally offset from each other in a direction perpendicular to a longitudinal axis of the first bore. The body may also include a second bore oriented transversely to and in communication with the first bore. The detent mechanism may include an engaging member and a biasing element operable to urge the engaging member towards the first bore. The engaging member and the biasing element may be disposed within the second bore.

The various aspects may also include one or more of the following features. The first bore portion may include a first orientation-defining structure. The plunger tip may include a second orientation-defining feature, and the first orientation-defining feature and the second orientation-defining feature may cooperate to radially orient the plunger tip in a selected position. The first orientation-defining feature may be a first planar surface, and the second orientation-defining feature may be a second planar surface. Further, the first planar surface and the second planar surface may contact each other to align the plunger tip within the second longitudinal bore. The first alignment feature may include at least one enlarged portion extending outwardly from the body. An outer dimension of the enlarged portion may be larger than a dimension defined between the tabs formed on the cartridge holder such that an interference fit is formed between the enlarged portion and the tabs.

The detent mechanism may include an engaging member and a biasing element operable to urge the engaging member towards the first bore. The engaging member and the biasing element may be disposed within the second bore. The plunger tip wrench may also include a bore disposed transversely to and in communication with the second longitudinal bore. The detent mechanism may be disposed within this bore. The plunger tip may include a recess, and the biasing element may urge the engaging member into the recess of the plunger tip to releasably retain the plunger tip at a desire location within the second longitudinal bore of the plunger tip wrench. The cartridge holder may have an arcuate shape. The plunger may include a first coupling component, and the plunger tip may include a second coupling component. The first coupling component and the second coupling component may cooperate to releasably couple the plunger tip to the plunger. An end of the plunger may include a bore and an annular groove formed in an interior surface of the bore. A mating end of the plunger tip may include a pair of prongs laterally offset from each other and a protrusion formed on each of the prongs. When the pair of laterally offset prongs is received into the bore formed in the end of the plunger, the protrusions formed on the pair of prongs may be received into the annular groove.

The various aspects may further include one or more of the following features. The plunger tip may be releasably retained within a plunger tip wrench. Locating a plunger tip in alignment with the plunger may include coupling the plunger tip wrench to a mount of the IOL injection device such that the plunger tip is aligned and in a desired orientation relative to the plunger. Extending the plunger from an initial position towards the plunger tip to an engagement position may include actuating a motor of the IOL injection device to extend the plunger from the initial position to the engagement position. A position of the plunger may be detected utilizing a back electromotive force (EMF) of the motor. A position of the plunger detected by the back EMF may be within a range of a negative error position corresponding to a negative positional error and a positive error position corresponding to a positive positional error. Locating a plunger tip in alignment with the plunger may include locating an end of the plunger tip at a position corresponding the negative positional error such that the plunger contacts the plunger tip within the entire range between the negative error position and the positive error position when the plunger is extended from the initial position to the engagement position. The back EMF may be monitored to detect a fault condition.

The details of one or more implementations of the present disclosure are set forth in the accompanying drawings and the description below. Other features, objects, and advantages will be apparent from the description and drawings, and from the claims.

BRIEF DESCRIPTION OF THE DRAWINGS

FIG. 4 illustrates a removable plunger tip according to some implementations of the present disclosure.

FIGS. 6 and 7 are cross-sectional views of an example IOL injection device showing the actuating apparatus in a fully retracted position and in a partially extended position, respectively.

FIGS. 12-14 are various views of another example plunger tip wrench.

FIG. 15 is a cross-sectional view of the plunger tip wrench shown in FIGS. 12-14.

FIG. 28 is a partial cross-sectional view of mating ends of an example plunger and example plunger tip.

FIGS. 29 and 30 are cross-sectional views of an example IOL injection device showing the installation of a plunger tip onto the plunger of the IOL injection device.

DETAILED DESCRIPTION

Figure 1:
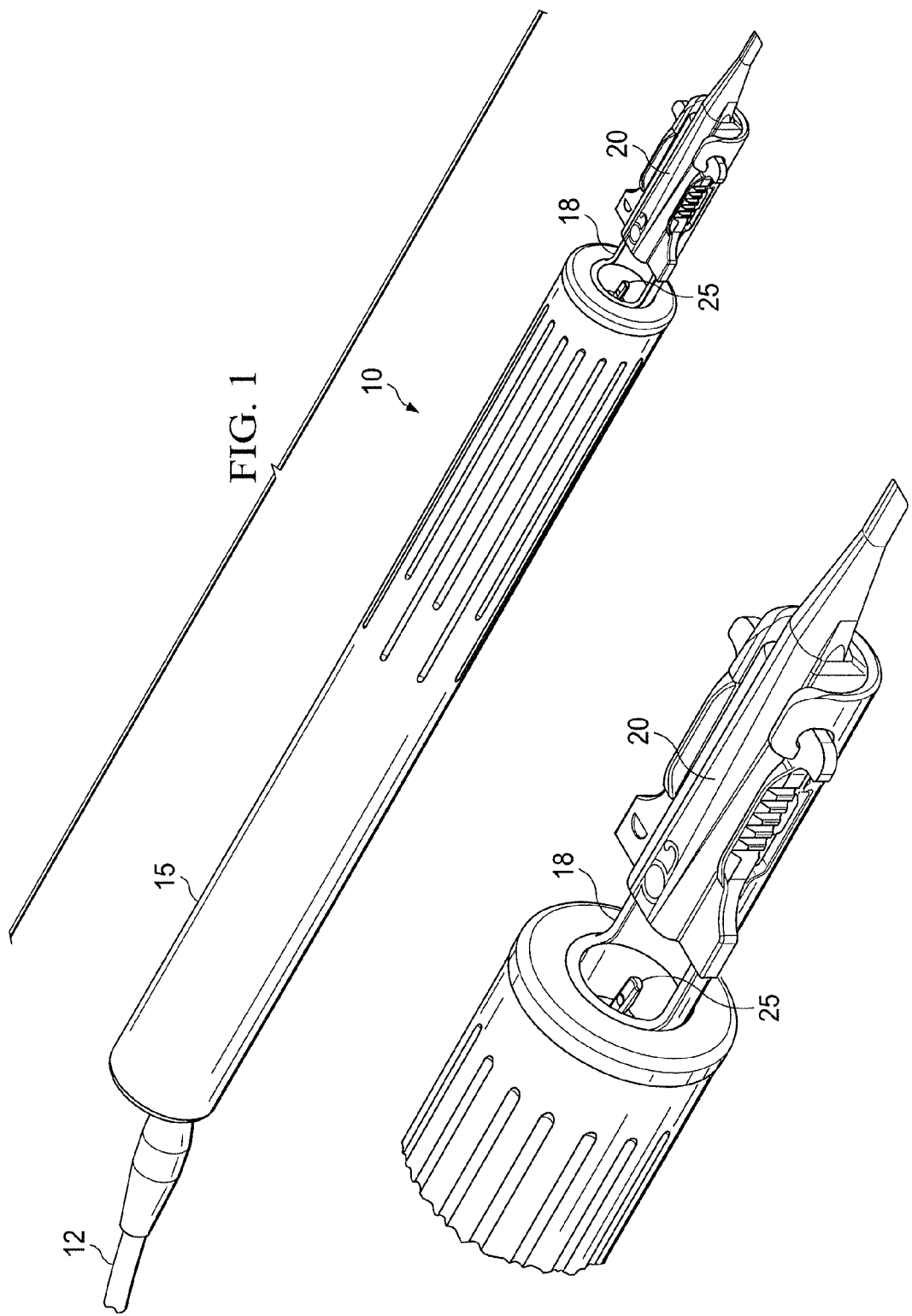
FIG. 1 is a perspective view of an example IOL injection device, with an insertion cartridge installed.

The present disclosure is directed to, among other things, devices, systems, and methods of coupling a plunger tip onto a plunger of an intraocular lens (IOL) injection device. FIG. 1 shows an example handheld IOL injection device 10 for implanting an IOL into the anterior capsule of the eye. As pictured, IOL injection device 10 includes a cable assembly 12 that carries power and/or control signals from a separate user console (not shown), although some implementations may include one or more batteries in the main housing 15 to provide electrical power to the device and/or one or more switches or other user input devices to control the operation of the device. The pictured IOL injection device 10 may also include a cartridge mount 18, which holds a removably mounted insertion cartridge 20. As will be explained in further detail below, the insertion cartridge 20 in some implementations is a disposable polymeric component adapted to accommodate an unfolded IOL lens and to fold and displace the lens as a plunger tip 25 is translated forward from the body of the housing 15 and through the insertion cartridge 20. In some implementations, the cartridge mount 18 may comprise a "nosecone" that includes a unique cutout to accommodate the IOL cartridge and that is press-fitted to an inner shell of the housing 15. In some implementations, the nosecone may be formed from metal.

Figure 2:
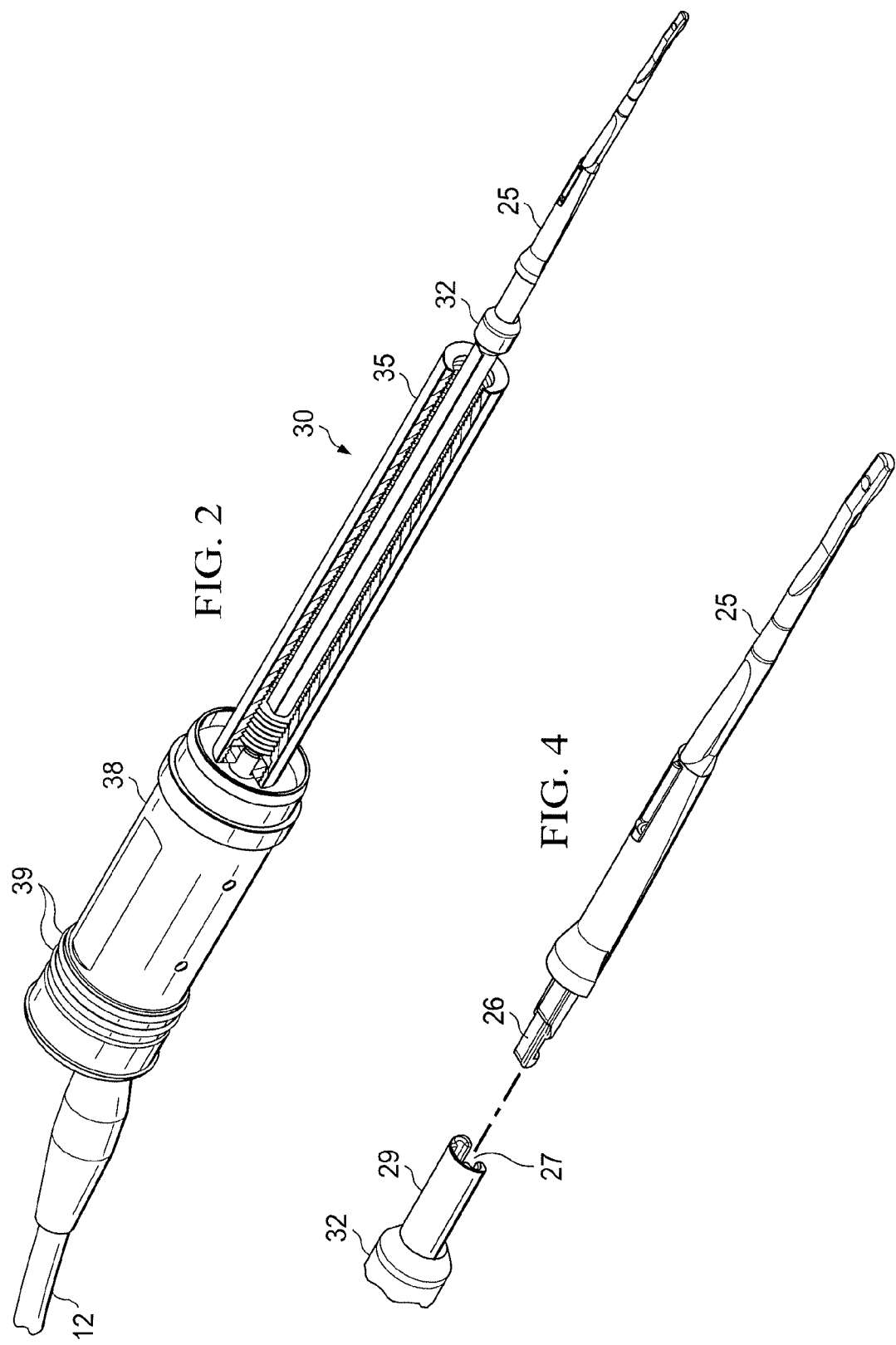
FIG. 2 is a perspective view of an actuating mechanism of an example IOL injection device.
Figure 3:
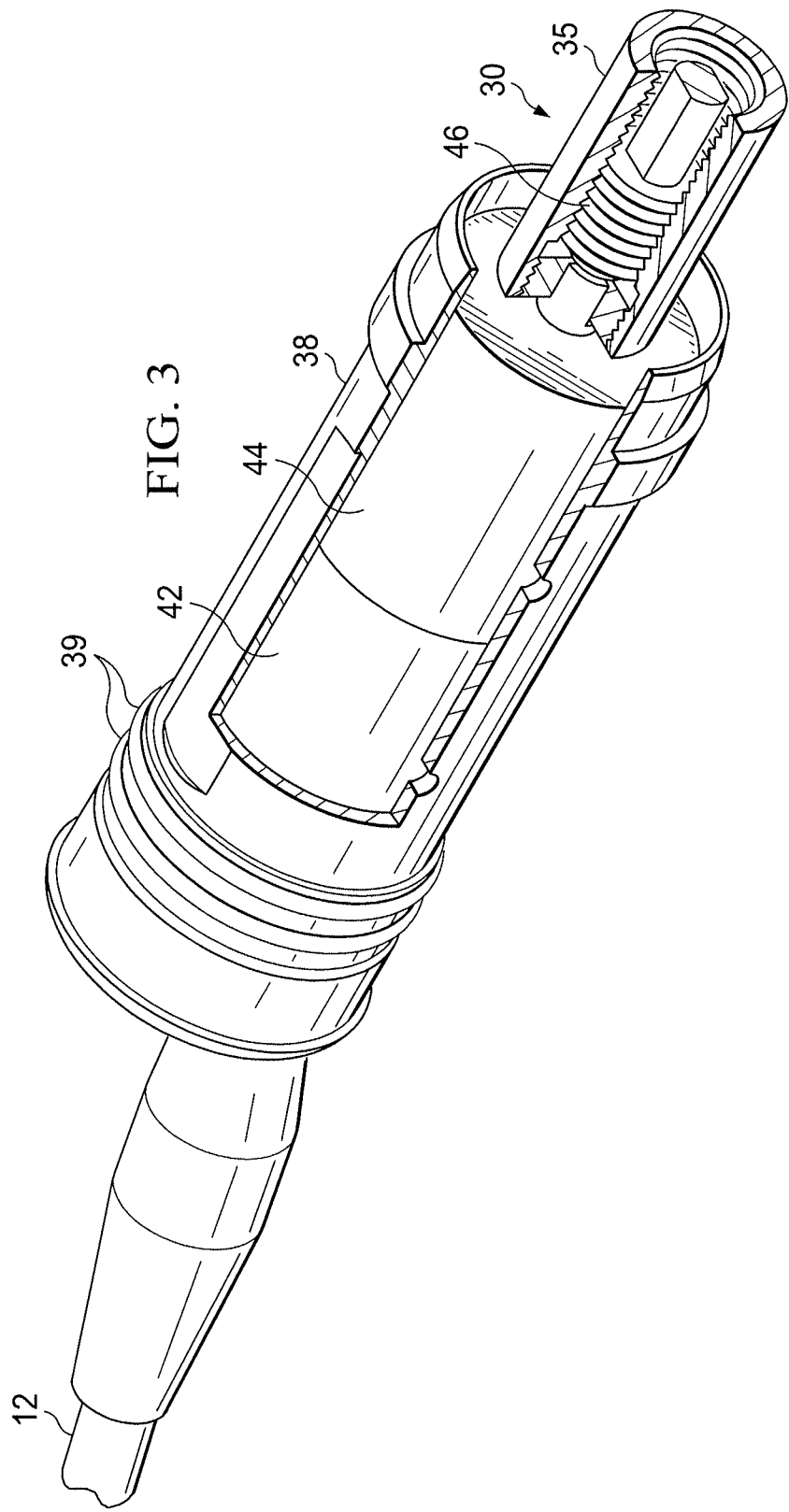
FIG. 3 is a partial cutaway view of the actuating mechanism of FIG. 2 showing an electric drive system thereof.
Figure 5:
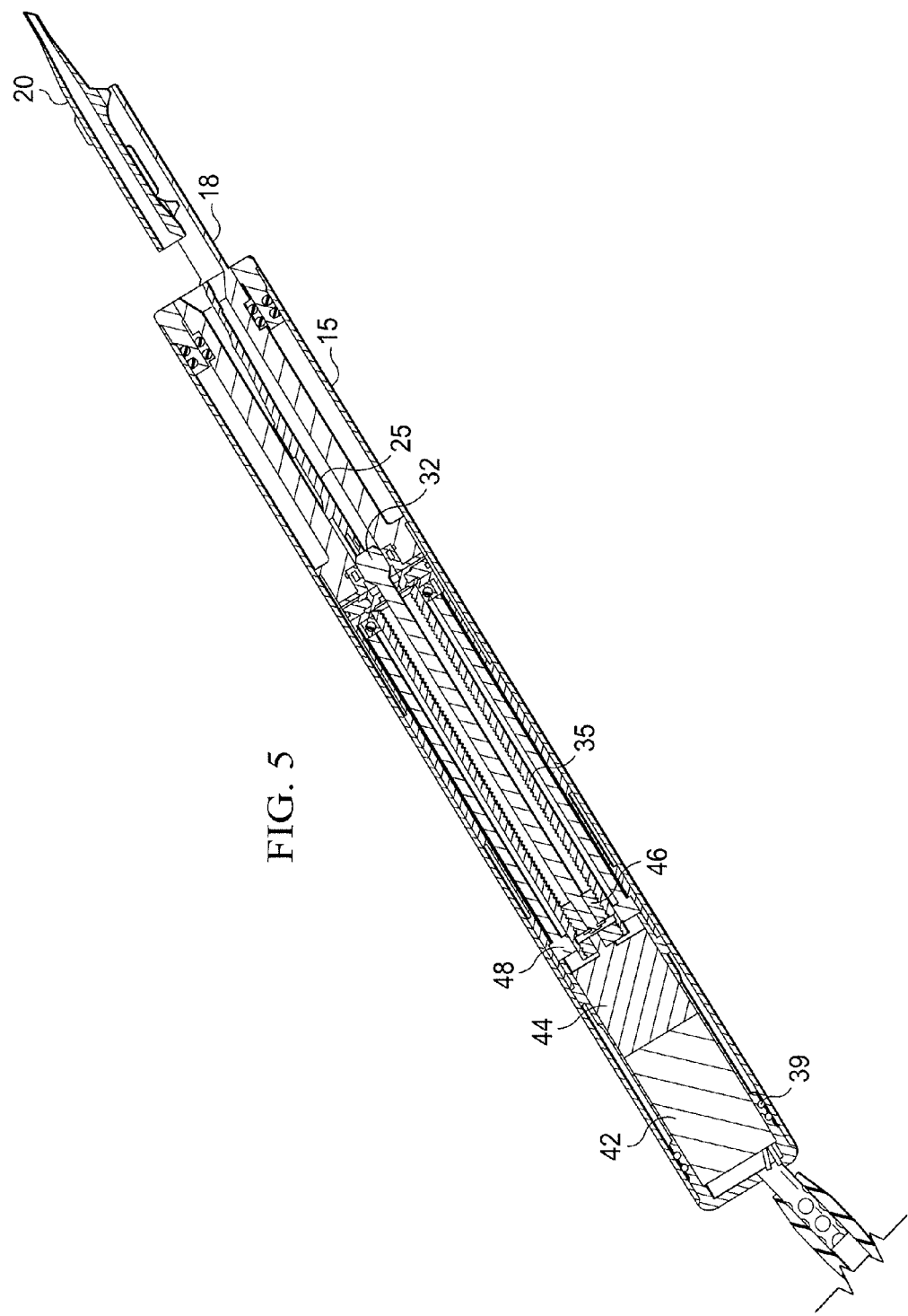
FIG. 5 is a cross-sectional view of an example IOL injection device.

FIG. 2 illustrates a partially cut-away view of an example IOL injection device, such as IOL injection device 10, showing the internal workings of an actuating assembly 30 for linearly translating the plunger tip 25 along the primary axis of the device's housing. FIGS. 3 and 4 provide details of the assembly of FIG. 2, and FIG. 5 illustrates a cross-sectional view of the IOL injection device 10.

In the illustrated implementation, the actuating assembly may include, in addition to the plunger tip 25, a plunger 32 configured for longitudinal translation inside an internally threaded tubular coupler 35 and an electric drive system 38. As shown in FIGS. 3 and 4, the electric drive system 38 may include an electric motor 42 and gear set 44 disposed within a weldment and configured to rotate the tubular coupler 35, which is held in place by a polymeric coupler sleeve 48. The internal threads on the tubular coupler 35 engage an externally threaded male coupler 46 at the rear end of the plunger 32, forcing linear translation of the plunger 32 and plunger tip 25 within the tubular coupler 35, in response to activation of the drive system 38. The internal threads of the tubular coupler 35 and/or the threads of the male coupler 46 are coated with a lubricant (which may be a dry film coating such as Endura 200TX, Brycoat WS2, Teflon/FEP, or the like) to minimize friction. O-rings 39, which may be formed from an elastomer, provide a seal to the tubular housing 15, preventing moisture and/or other contaminants from reaching the interior of the housing 15.

In some implementations, the electric drive system 38 may include a brushless DC motor 42 for providing rotational torque to the gear set 44, which in turn rotates the tubular coupler 35 to extend or retract the plunger 32. The gear set 44 is effective to reduce the angular velocity of the motor according to a pre-determined reduction ratio. For example, in some implementations, a gear ration of 125:1 may be used. This increases the available torque from the drive system 38, and slows the linear motion of the plunger 32 to a speed appropriate for the IOL injection procedure.

In some implementations, plunger tip 25 may be removable from the plunger 32, as shown in FIG. 4. In some implementations, the plunger tip 25 may include a disposable plastic sleeve that attaches to the forward end of the plunger 32, in some cases according to a "snap-fit" mechanism. The end of the plastic sleeve that engages the IOL may be more compliant than a bare metallic plunger would be, and may have a smooth surface finish, thus avoiding damage to the IOL as it is pushed through the insertion cartridge 20 and into the eye. The use of a disposable plastic sleeve may also ease reprocessing of the IOL injection device 10 between uses.

FIG. 4 shows that, in coupling the plunger tip 25 to the plunger 32, an end 26 of the plunger tip 25 may be received into a slot 27 formed in an end 29 formed in the plunger 32, according to some implementations. In other implementations, such as that shown in FIG. 28, an end 160 of the plunger tip 25 may be include prongs 162 separated by a gap 164. Additionally, an arcuate protrusion 166 may be formed on an outer surface of each prong 162. An end 168 of the plunger 32 may include a passage 170 formed in an end 172 thereof and an annular groove 173 formed within the passage 170. The passage 170 may be stepped, such that a first portion 174 of the passage 170 has a smaller diameter than a second portion 176. Further, the diameter of the first portion 174 may be smaller than an outermost dimension of the arcuate protrusions 166.

During coupling, the end 160 of the plunger tip 25 is received into the passage 170. As the arcuate protrusions 166 engage an interior surface of the first portion 174 of the passage 170, the prongs 162 are flexed towards each other. When the arcuate protrusions 166 reaches the annular groove 173, the arcuate protrusions 166 are received into the annular groove 173, and the prongs 162 spring back to their at-rest position, interlocking the plunger tip 25 with the plunger 32.

FIGS. 6-9 provide additional details of an exemplary IOL injection device according to some implementations. FIGS. 6 and 7 illustrate a longitudinal cross-section of IOL injection device 10 with the plunger 32 in fully retracted and in partially extended positions, respectively. In the partially extended position illustrated in FIG. 7, the plunger tip 25 is just beginning to pass into the insertion cartridge 20.

As seen in FIG. 6, the male coupler 46, which is bored and "keyed" along its axis to accommodate the plunger 32, is held in place with a retaining ring 52 that clips into a circumferential groove at the rear end of the plunger 32, thus securing the male coupler 46 in place. At the opposite end of the tubular coupler 35, a bearing assembly 54, held in place by a polymeric bearing sleeve 56, holds the tubular coupler 35 in a position concentric to the housing and facilitates smooth rotational motion of the tubular coupler 35. A compression seal 58, comprising an elastomer jacket and a metal channel ring, provides a seal to prevent moisture ingress. The plunger 32, which has a cross section with two flat faces, is prevented from rotating relative to the housing by an orientation insert 60, which is held in place by pins 62.

Figure 8A:
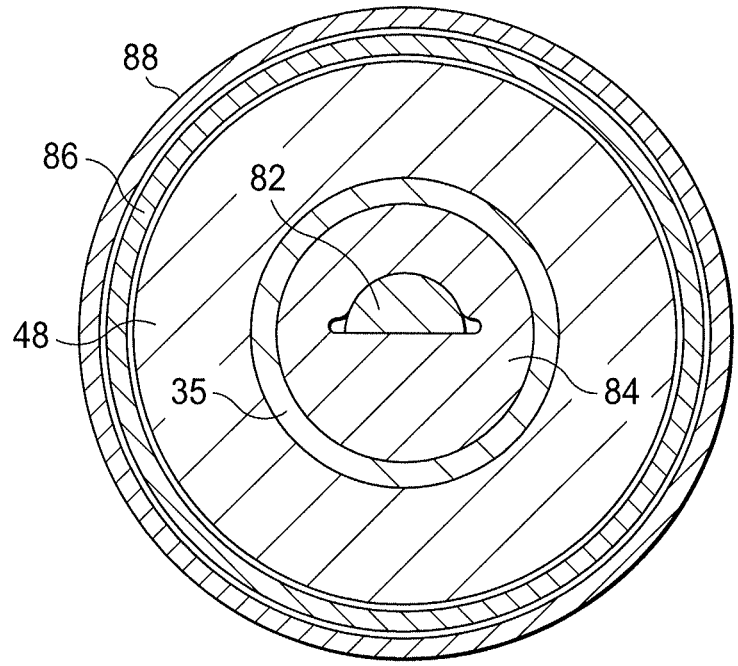
FIGS. 8A and 8B are cross-sectional views of alternative examples of the device of FIGS. 6 and 7, taken along line VIII.
Figure 8B:
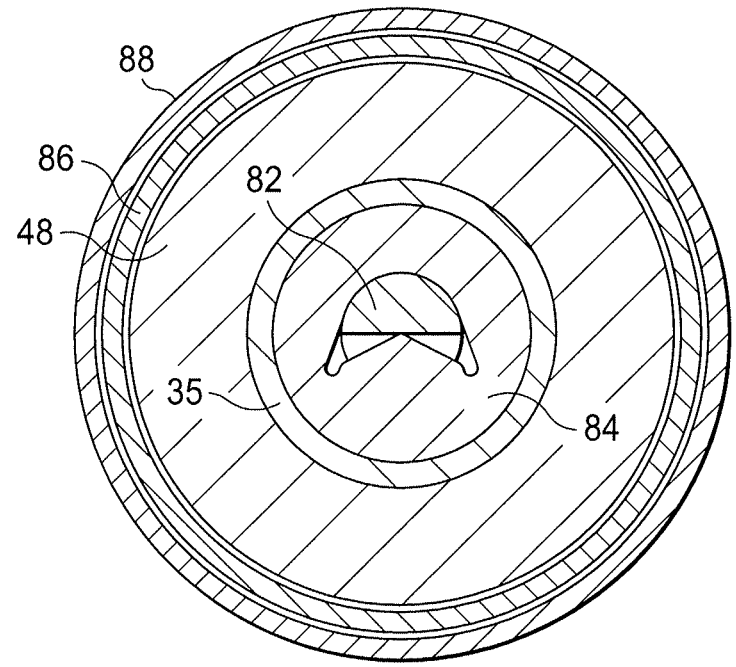

FIGS. 8A and 8B provide cross-sectional views, corresponding to the section indicated as "VIII" in FIG. 7, of two different implementations of IOL injection device 10. As seen in each of these figures, a drive shaft 82 extending from the gearbox 44 engages a keyed endplate 84 of tubular coupler 35 to transfer rotational torque of the drive system 38 to the tubular coupler 35. Tubular coupler 35 is surrounded by coupler sleeve 48 and an inner shell 86 and outer shell 88 of the housing 15. In the example shown in FIG. 8B, the endplate 84 of tubular coupler 35 is slotted to subtend an arc that exceeds the portion of the slot occupied by the drive shaft 82. This allows the drive shaft to rotate freely for part of a rotation upon a reversal in direction. This feature may facilitate start-up of the electric motor in some embodiments, and may also be used in some embodiments to calibrate a monitoring circuit for a "no load" condition. As will be explained in further detail below, this calibration may be used to establish one or more thresholds for use in fault detection.

Figure 9:
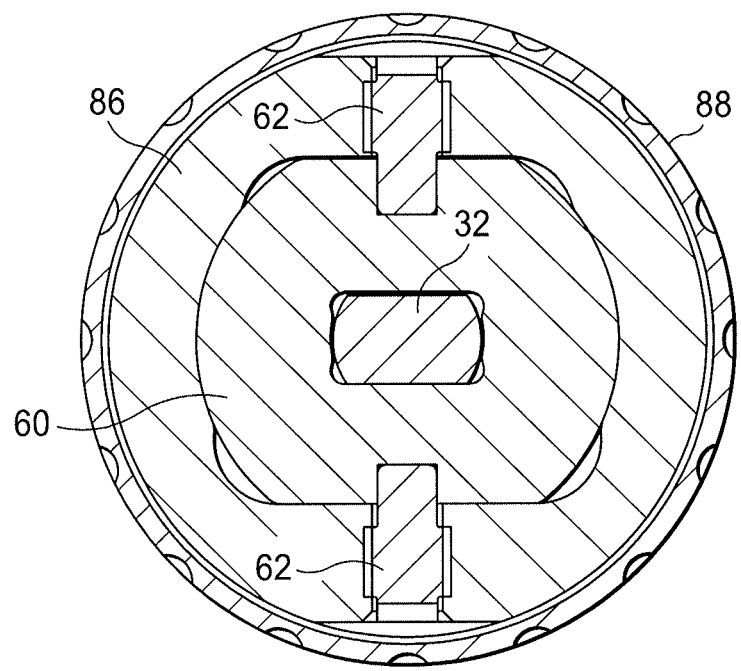
FIG. 9 is cross-sectional view of the IOL injection device of FIGS. 6 and 7, taken along line IX in FIG. 7.

FIG. 9 provides a cross-sectional view of some implementations of IOL injection device 10, corresponding to the section indicated as "IX" in FIG. 7. As noted above, plunger 32 may have a non-circular cross section, and may be held in place by orientation insert 60, which is in turn secured into position within the inner shell 86 and outer shell 88 of the housing by retaining pins 62. Because the plunger 32 is thus prevented from rotating, relative to the housing, rotation of tubular coupler 35 by the electric drive system 38 is converted into translational displacement of plunger 32 along the axis of the IOL injector device, as shown in FIGS. 6 and 7.

Figure 10:
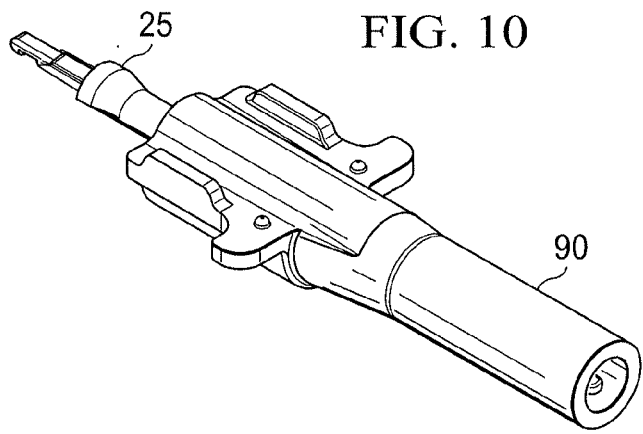
FIG. 10 shows an example plunger tip wrench.
Figure 11:
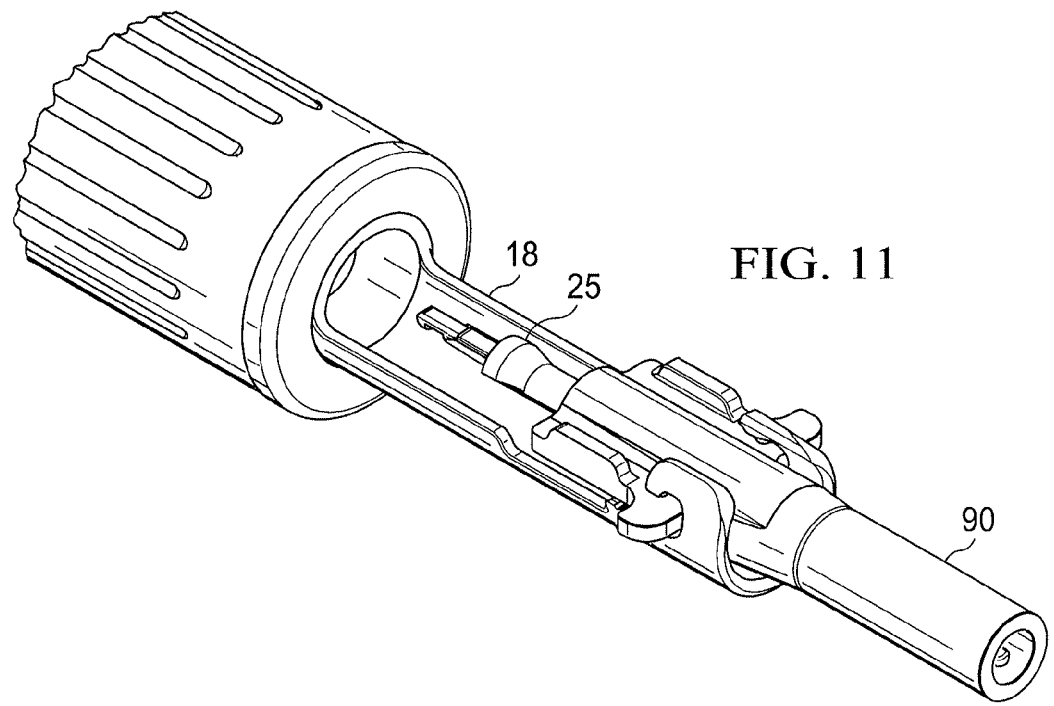
FIG. 11 shows the example plunger tip wrench of FIG. 10 coupled to an example IOL injection device.
Figure 12:
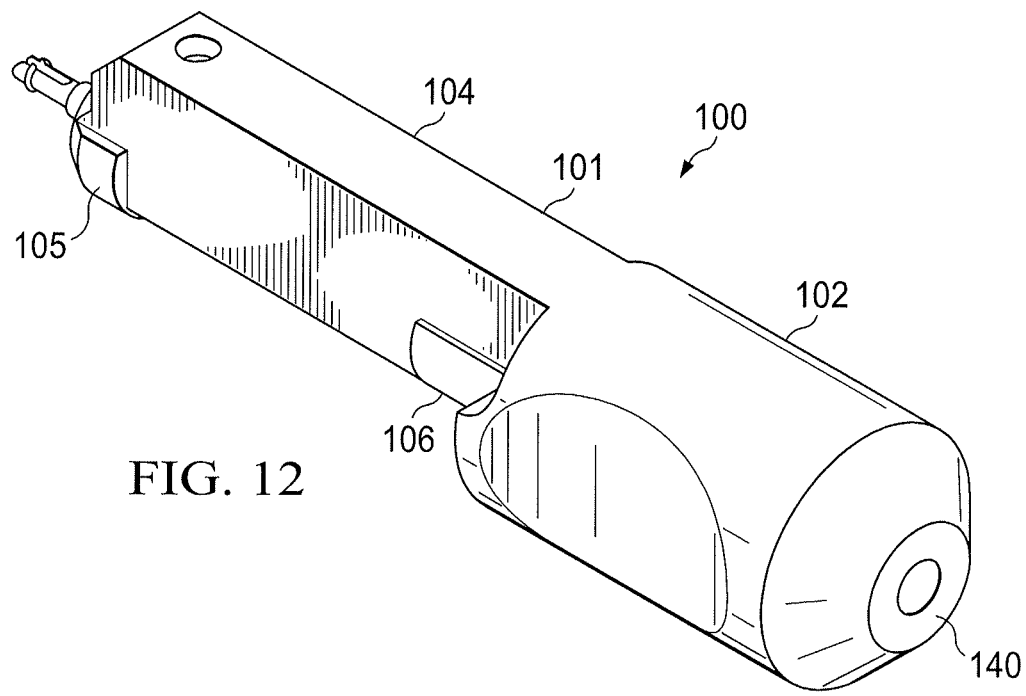
Figure 13:
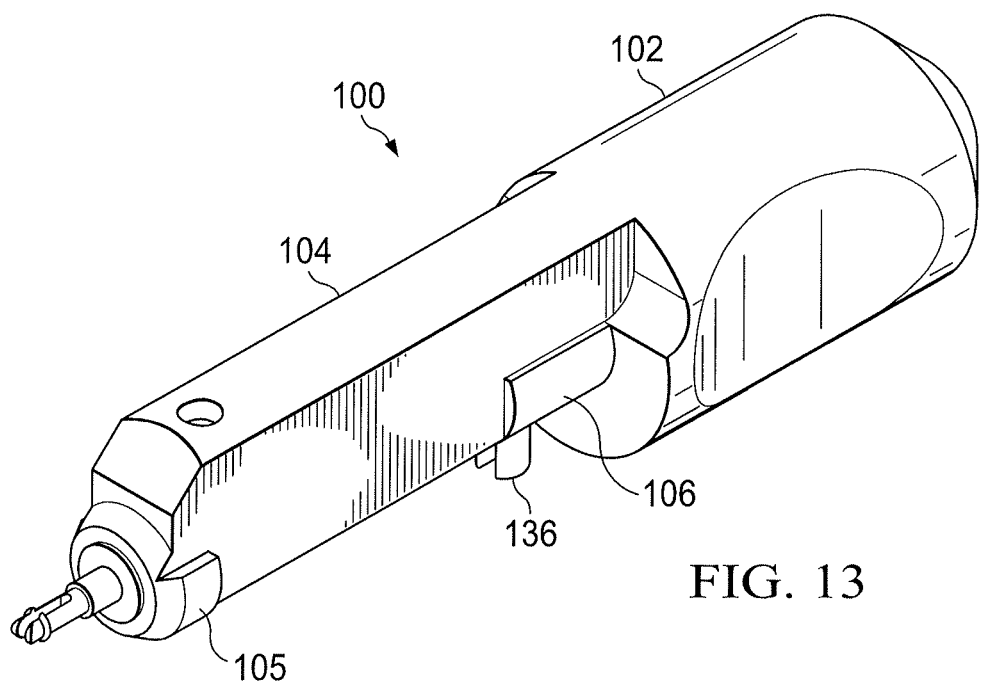

As shown above, in some implementations, an IOL injector device may include a plunger assembly. The plunger assembly may include two or more parts, including the plunger 32 and a plunger tip 25. In some embodiments, plunger tip 25 may comprise a removable plastic sleeve that snap-fits onto the plunger 32, and may be disposable after use. In some embodiments, a plunger tip wrench, may be used to install the plastic plunger tip 25 onto the plunger 32. FIG. 10 illustrates an exemplary plunger tip wrench 90 with a plunger tip 25 held inside. FIG. 11 shows the plunger tip wrench 90 installed onto the cartridge mount 18.

A plunger tip wrench may be used to install the plunger tip onto the plunger of the IOL injection device. FIG. 10 illustrates an example plunger tip wrench 90 with a plunger tip 25 held thereinside. FIG. 11 shows the plunger tip wrench 90 installed onto the cartridge mount 18. The plunger tip wrench 90 may be secured onto the cartridge mount 18 in the same manner as the insertion cartridge 20. In some embodiments, the plunger tip 25 is automatically installed onto the plunger 32 in response to user activation of an installation mode. For example, after the user pushes an appropriate button or other control on the device or on an accompanying operator console, the plunger 32 may be actuated at a designated speed to couple the plunger 32 with the plunger tip 25. In some implementations, the plunger 32 may have a snap fit with the plunger tip 25. Further, in some implementations, the plunger tip 25 may be disposable after a single use. This actuation may be followed by retraction of the plunger 32 to its original starting position at a designated speed. The retraction pulls the plunger tip 25 from the plunger tip wrench 90, which may then be removed and replaced with a loaded IOL insertion cartridge 20. As will be discussed in further detail below, both operations may automatically terminated responsive to monitoring of the counter-electromotive force (often called "back EMF") produced by the spinning electric motor 42.

FIGS. 12-15 show another example plunger tip wrench 100 according to some implementations. The plunger tip wrench 100 is operable to load a plunger tip 25 to an intraocular lens (IOL) injection device. The wrench 100 includes a housing 101 defining a grip portion 102, an elongate portion 104, and alignment features 105, 106 formed on the elongate portion 104. As is explained in more detail below, the alignment features 105, 106 are operable to orient and secure the wrench 100 within a mounting structure disposed at an end of an IOL injection device.

In some instances, the housing 101 is formed from titanium. In other instances, the housing 101 is formed from stainless steel. However, the housing 101 may be formed from other materials. For example, the housing 101 may be formed from other metals, such as other types of steels. Still further, the housing 101 may be formed from any other suitable material. Also, the plunger tip 25 may be formed from stainless steel, titanium, or any other suitable material.

Figure 16:
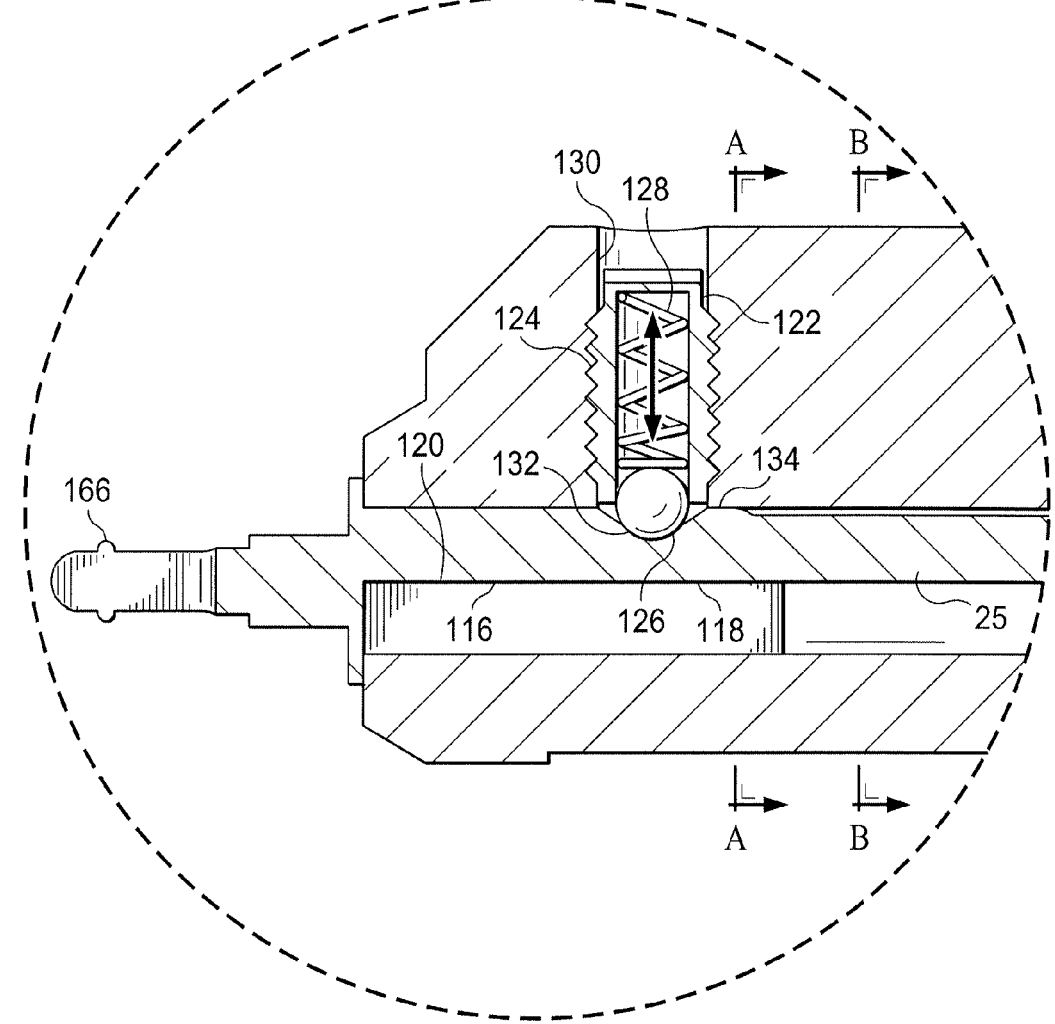
FIG. 16 is a detail view of a portion of the plunger tip wrench shown in FIG. 15.
Figure 17:
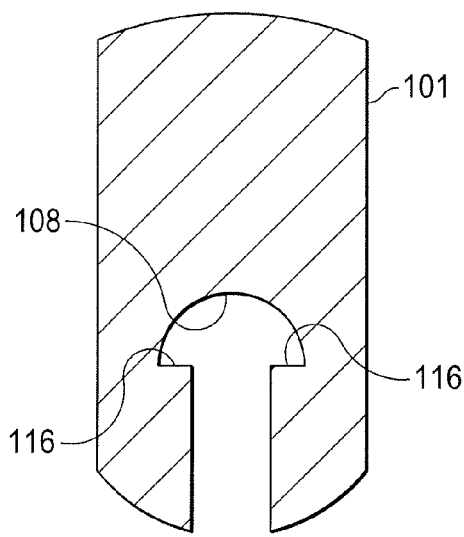
FIGS. 17 and 18 are cross-sectional view of the plunger tip wrench taken along lines A-A and B-B, respectively, shown in FIG. 16.
Figure 18:
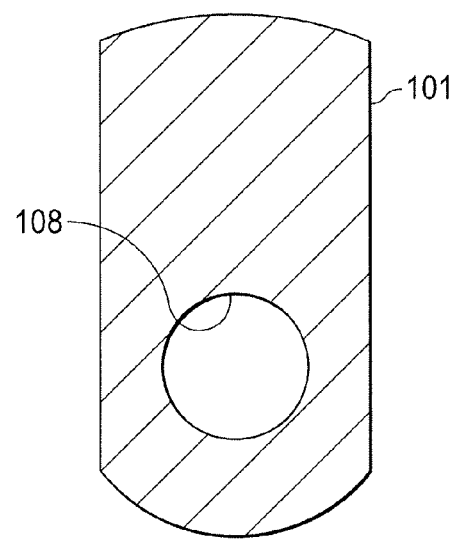
Figure 19:
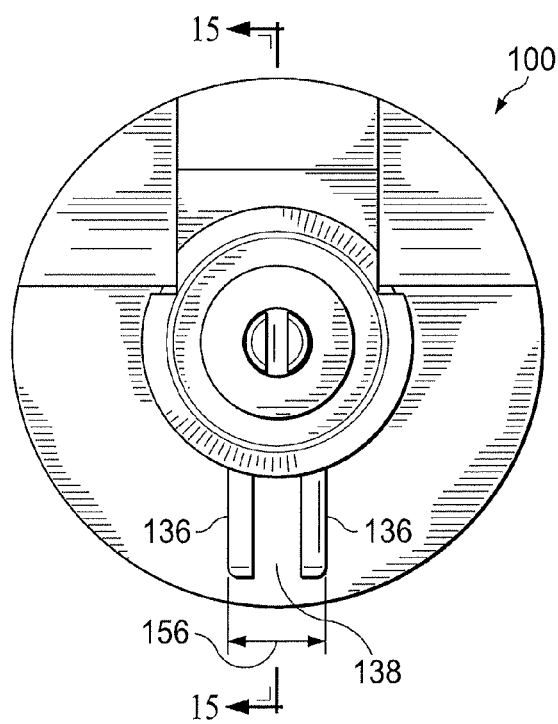
FIG. 19 is a front view of the example plunger tip wrench shown in FIGS. 12-14.
Figure 20:
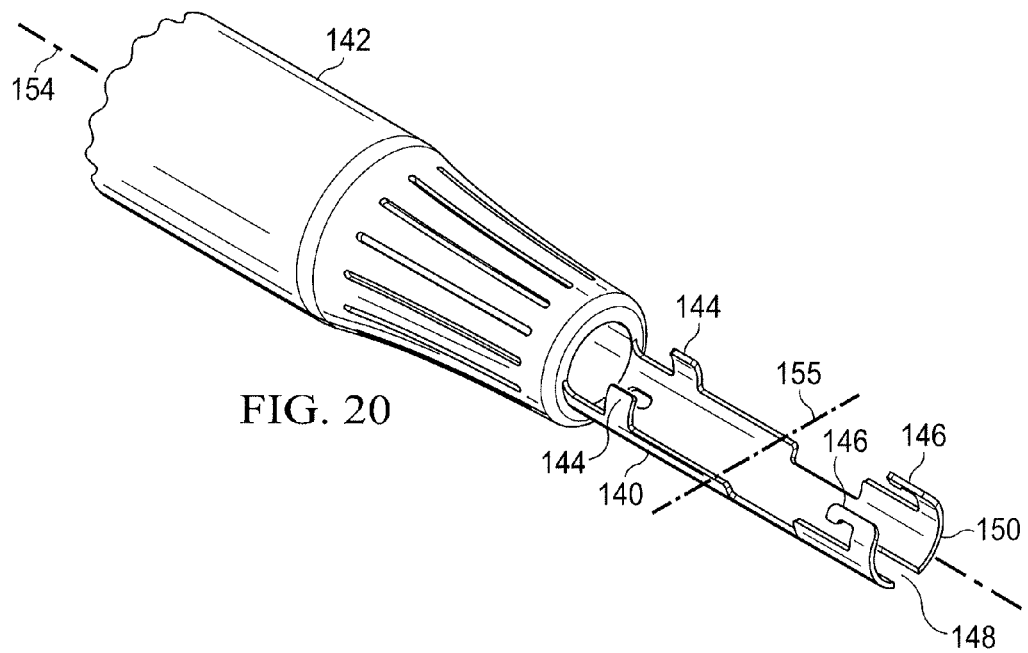
FIGS. 20 and 21 show perspective views of a nosecone of an example IOL injector device.
Figure 21:
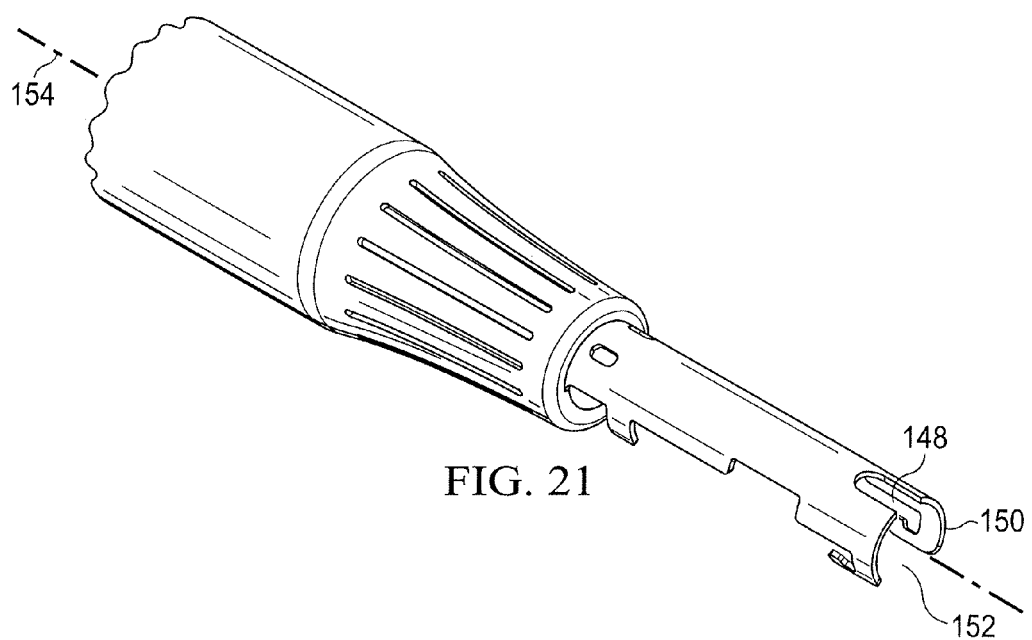

As shown in FIGS. 15 and 16, the wrench 100 also includes a bore 108 for receiving a plunger tip, such as the example plunger tip 25. FIG. 16 shows a partial detail view of the cross-sectional view shown in FIG. 15. In some instances, the bore 108 may include a first portion 112 and a second portion 114. FIGS. 17 and 18 are cross-sectional views along lines A-A and B-B, respectively, in FIG. 16 showing details of the shapes of the first portion 112 and second portion 114 of the bore 108, respectively. As shown in FIG. 17, the first portion 112 may include surfaces 116. In the example shown, the surfaces 116 are planar surfaces that cooperate with a planar surface (e.g., planar surface 120) included on the plunger tip 25 to orient the plunger tip 25 in a desired orientation. In the illustrated example, the surfaces 116 reduce the cross section of the bore 108 compared to the second portion 114. While the example plunger tip wrench 100 is shown as including planar surfaces 116 to orient the plunger tip 25 within the bore 108, the scope of the disclosure is not so limited. Rather, the plunger tip wrench 100 may include any structure operable to orient the plunger tip 25 in a desired orientation.

Referring again to FIGS. 15 and 16, as shown, the plunger tip wrench 100 may include a detent mechanism 122 operable to releasably retain the plunger tip 25 within the plunger tip wrench 100. In some instances, the detent mechanism 122 may include a retainer 124, an engaging member 126, and a biasing element 128 disposed in the retainer 124 operable to bias the engaging member 126 into the bore 108. In some instances, the engaging member 126 may be spherical member. In some instances, the biasing element 128 may be a spring. Further, in some instances, retainer 124, engaging member 126, and the biasing element 128 may be formed from stainless steel. However, the detent mechanism 122 and the components thereof may be formed from any suitable material.

In some instances, the detent mechanism 122 is received within a bore 130. In some instances, the detent mechanism 122 may be retained in the bore 130 via a threaded connection between an exterior surface of the retainer 124 and a threaded interior surface of the bore 130. However, the detent mechanism 122 may be retained within bore in any desired manner. For example, an interference fit between the detent mechanism 122 and the bore 130 may be utilized. In some instances, an adhesive, retaining ring, or any other manner of retaining the detent mechanism 122 may be used. Further, while an example detent mechanism 122 is explained, the disclosure is not so limited. Rather, any suitable manner of releasably retaining the plunger tip 25 may be used.

The engaging member 126 may be received into a recess 132 formed in the plunger tip 25. During insertion of the plunger tip 25 into the bore 108 of the wrench, an exterior surface 134 of the plunger tip 25 contacts the engaging member 126 to displace the engaging member 126 into the retainer 124. Once the plunger tip 25 is located at a position in which the engaging member 126 aligns with the recess 132 formed in the plunger tip 25, the biasing element 128 urges the engaging member 126 into the recess 132, causing the plunger tip 25 be retained within the bore 108 at a desired position.

Figure 22:
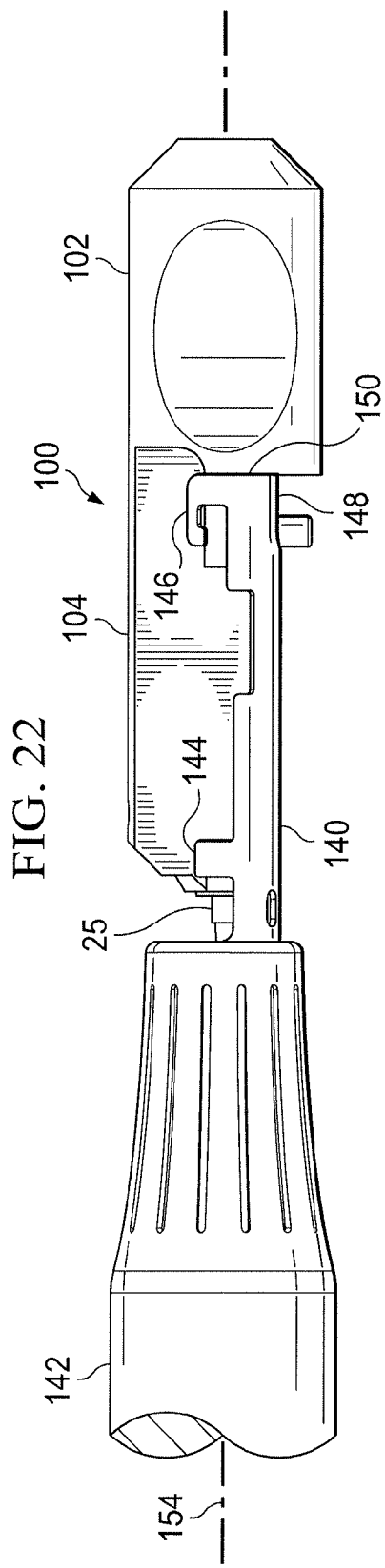
FIG. 22 shows the example plunger tip wrench of FIGS. 12-14 received within a cartridge mount of the example nosecone shown in FIGS. 22 and 22.

Referring to FIGS. 12-14 and FIGS. 19-22, the wrench 100 includes alignment features 105, 106 and protrusions 136. The protrusions 136 are lateral offset from each other forming a gap 138. As shown in FIG. 22, the wrench 100 is received within a cartridge mount 140 extending from an end of a nosecone 142. The nosecone 142 may be coupled to or form part of an end of an IOL injection device, such as the IOL injection device 10. The cartridge mount 140 may include tabs 144 and tabs 146. The holder may also include a slot 148 defined in a leading edge 150 of the cartridge mount 140.

The plunger tip wrench 100 may be received into the carriage mount 140. For example, the plunger tip wrench 100 may be received into the carriage mount 140 by sliding the plunger tip wrench 100 through opening 152 of the cartridge mount 140 along a longitudinal axis 154 of the nosecone 142. The longitudinal axis 154 may also be the longitudinal axis of the IOL injection device. When the plunger tip wrench 100 is received in the cartridge mount 140, the tabs 144 align with and embrace the alignment feature 105, and the tabs 146 align with and embrace the alignment feature 106. In some instances, the alignment features 105 and/or 106 may have a dimension slightly larger than an interior dimension defined by the tabs 144 and/or 146. Thus, when the wrench 100 is received into the cartridge mount 140, the alignment features 105 and/or 106 may cause the tabs 144 and/or 146 to flex or otherwise expand outwardly, creating an interference fit between one or more of the alignment features 105, 106 and the associated tabs 144, 146.

The alignment features 105, 106 and the tabs 144, 146 cooperate to align the wrench 100 in the cartridge mount 140. Further, the alignment features 105, 106 and the tabs 144, 146 cooperate to prevent or substantially reduce pivoting of the wrench 100 within the cartridge mount 140 about an axis that is normal to the longitudinal axis 154, such as axis 155 shown in FIG. 20.

The protrusions 136 are received into the slot 148. The slot 148 may have a width that is smaller than the width 156 of the protrusions 136 (shown in FIG. 19). Thus, when the protrusions 136 are received within the slot 148, an interference fit results. Further, as a result of the gap 138, the restricted space within the slot 148 may cause the protrusions 136 to flex towards each other. The protrusions 136 and the slot 148 cooperate to angularly align the wrench 100 relative to the cartridge mount 140 about the longitudinal axis 154. Further, the resistance generated by the interference fit between the protrusions 136 and the slot 148 provides a resistive force that counteracts a force applied to the wrench 100 by the IOL injection device during installation of the plunger tip 25 to the plunger 32, described in more detail below.

Thus, the alignment features 105, 106; the tabs 144, 146; the protrusions 136; and the slot 148 cooperate to align and retain the wrench 100 within the cartridge mount 140. Further, these features cooperate to retain the wrench 100 within the cartridge mount 140 during installation of the plunger tip 25 to the plunger 32 of the IOL injection device.

Figure 23:
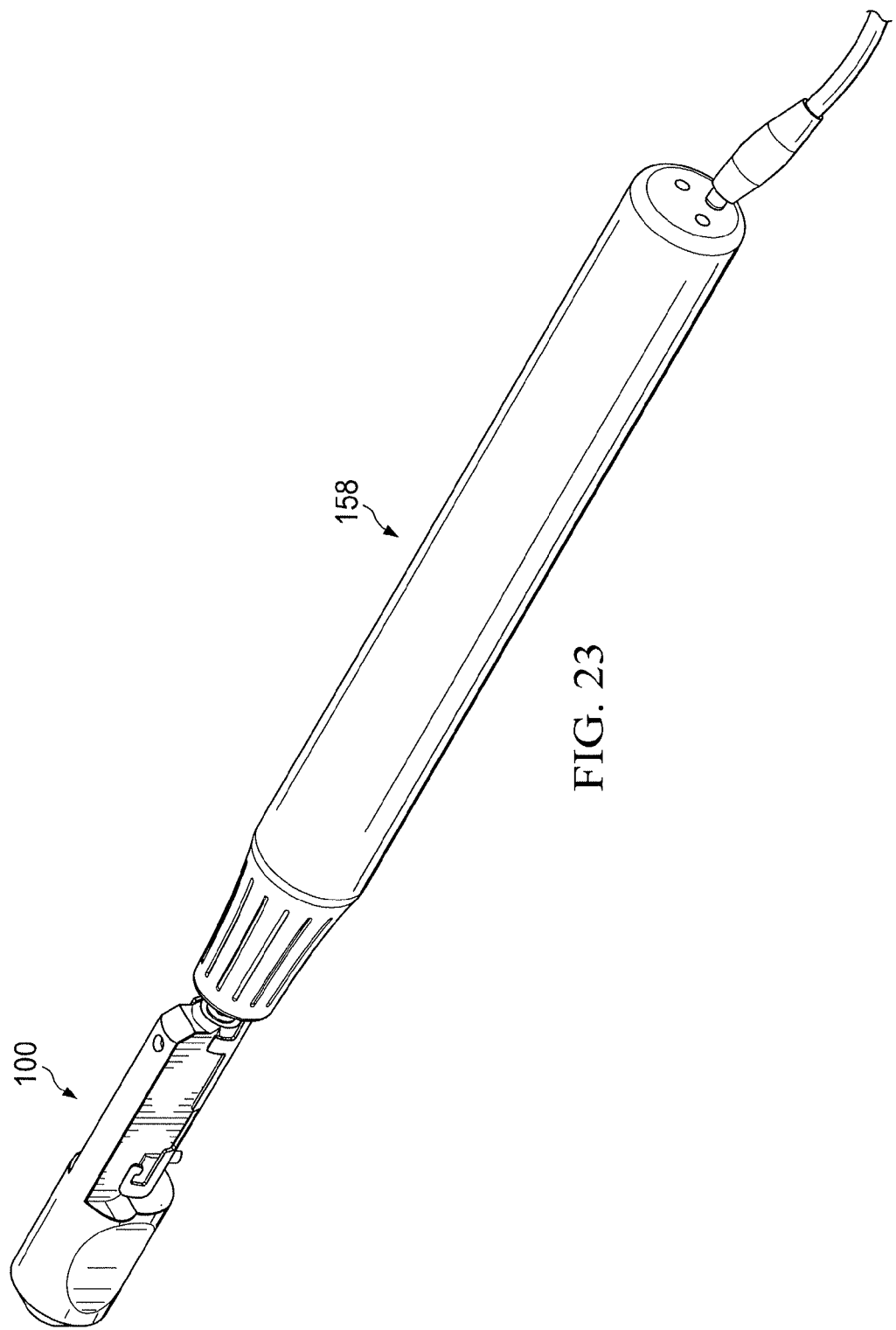
FIG. 23 is another example IOL injection device with a plunger tip wrench coupled thereto.

FIG. 23 shows an example plunger tip wrench 100 coupled to an example IOL injection device 158 according to some implementations. The IOL injection device 158 may be similar to the IOL injection device 10. Further, the IOL injection device may be a manual injector, an automated injector, or a semi-automated injection device. The following description describes an example IOL injection device within the scope of the present disclosure.

In some implementations in which a disposable plunger tip 25 is used, the plunger tip 25 and the insertion cartridge 20 may be provided with features so that the plunger tip 25 is automatically removed from the plunger 32 after use. In some of these embodiments, for example, the plunger tip 25 may be provided with one or more "teeth," or other protrusions, designed to engage with a corresponding catch on the insertion cartridge 20 when the end of the plunger tip 25 passes fully through the insertion cartridge 20. Once engaged, such a detention mechanism provides enough resistance to backwards movement of the plunger tip 25 so that the disposable sleeve ejects itself from the plunger. When the plunger 32 is fully retracted, the insertion cartridge 20 and the plunger tip 25 can be removed from the IOL injector as a unit, and discarded.

Figure 24A:
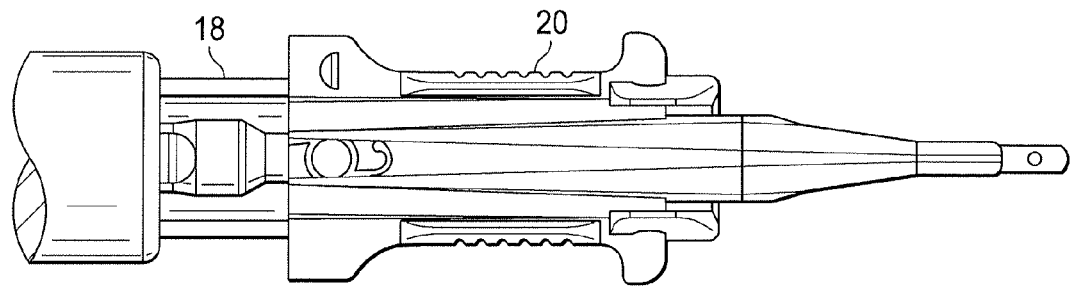
FIG. 24A shows an insertion cartridge mounted to a cartridge mount of an example IOL injection device.
Figure 24B:
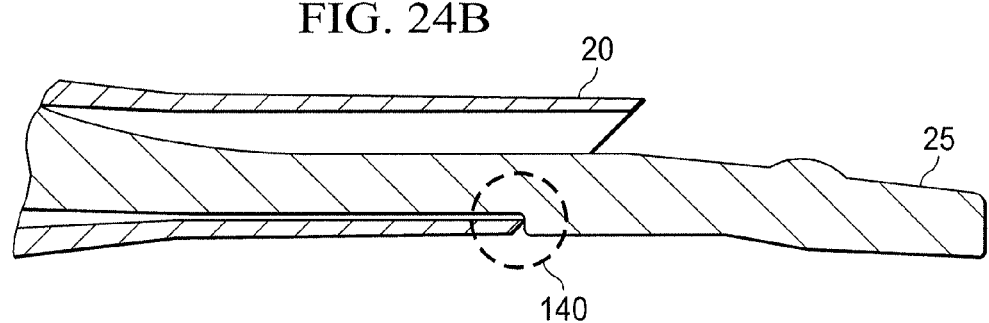
FIG. 24B shows a cross-sectional view of the insertion cartridge of FIG. A illustrating an example detention feature that may be used with a disposable plunger tip.

FIGS. 24A and 24B illustrate an exemplary detention mechanism, as discussed above. FIG. 24A provides a top view of an example plunger tip 25 fully inserted into insertion cartridge 20, and FIG. 24B illustrates an exemplary detention mechanism 140 that may be formed on the plunger tip 25. The detention mechanism 140 may include mating detention features on the plunger tip 25 and insertion cartridge 20. In the example implementation of FIG. 24B, a protrusion from plunger tip 25 engages a lower lip of the insertion cartridge 20 when the plunger tip 25 is in its fully extended position.

Figure 25:
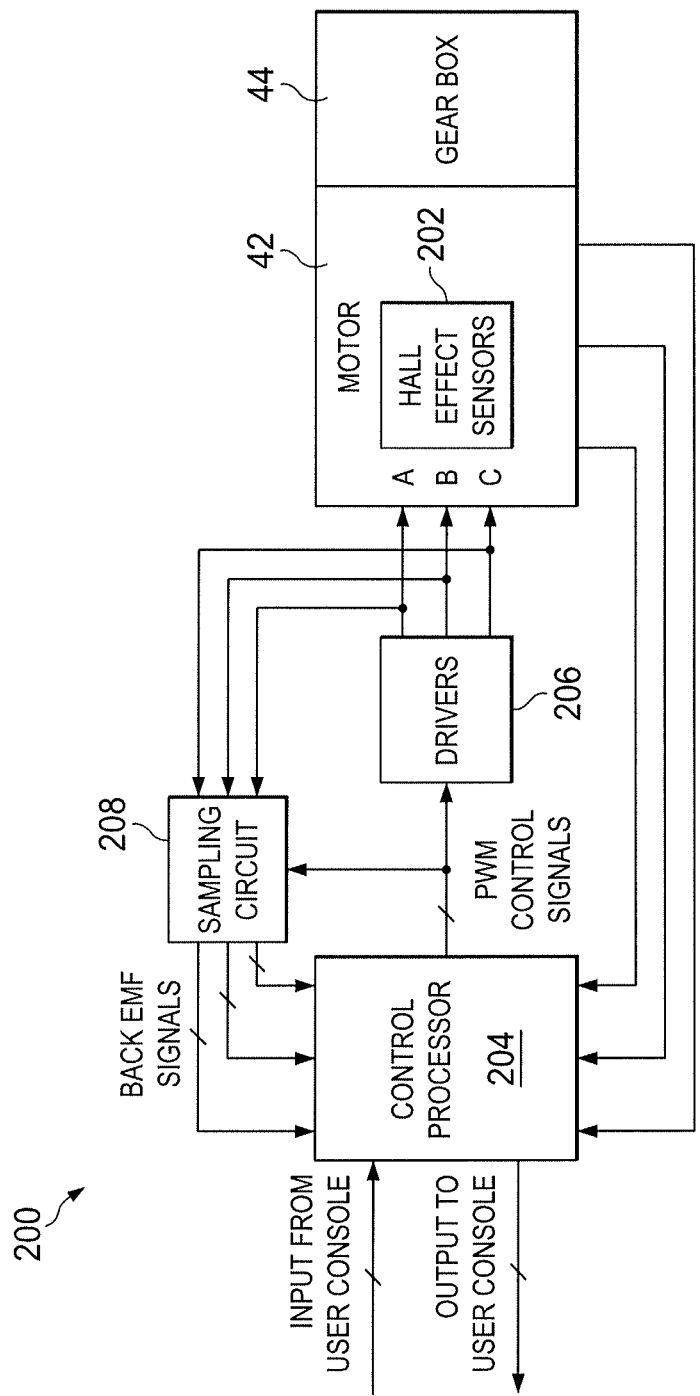
FIG. 25 is a schematic diagram of an example control circuit for an IOL injection device.

FIG. 25 illustrates an exemplary control circuit 200, according to some implementations, for controlling the operation of an IOL injection device. The pictured control circuit 200 is for a three-phase, brushless DC motor 42 that includes Hall-effect sensors 202. Although not shown in FIG. 25, the motor 42 may in some embodiments provide a neutral reference point; those skilled in the art will appreciate that the presence of a neutral terminal simplifies the measurement of back EMF, but is not absolutely necessary. In any case, those skilled in the art will appreciate that the circuit of FIG. 25 may be readily adapted for motors of different types, including brushed motors. In particular, those skilled in the art will appreciate that techniques for controlling a brushless DC motor without the use of Hall-effect sensor feedback are well known.

The control circuit 200 may include a control processor 204 which produces pulse-width modulated (PWM) control signals for commutating the motor 42, as well a driver circuit 206 for converting the digital control signals into analog drive signals applied to the stator winding inputs A, B, and C. Control circuit 200 further includes a sampling circuit 208 for detecting back EMF signals from the motor's rotor inputs A, B, and C; in some implementations, sampling circuit 210 may include analog-to-digital converters to convert the voltages at the motor inputs to digital signals for use by control processor 204. In some implementations, sampling circuit 208 may be synchronized to the PWM control signals produced by control processor 204, so that the back EMF for a given rotor input is only sampled when the drive for that input is floating. However, those skilled in the art will appreciate that in other implementations the motor inputs may be sampled over the entire duty cycle, and the back EMF signals isolated by digital processes in control processor 204. Those skilled in the art will appreciate that sampling circuit 208 may also include low-pass filters for each motor input signal in some implementations, although it will be understood that the delay caused by such low-pass filters should be considered when the motor is operating at a high speed.

In the pictured example implementation, control processor 204 has access to signals from Hall-effect sensors 202; these sensor outputs provide an indication of the motor's rotor position, and may be used by control processor 204 to control the timing of the PWM signals according to conventional techniques. Alternatively, zero-crossings of the back EMF signals may be detected, with the zero-crossing times used to synchronize the PWM signals controlling the current applied to the motor. Again, techniques for starting-up and controlling a sensorless brushless motor using back EMF signals are well known. Several such techniques are described, for example, in a master's thesis entitled "Direct Back EMF Detection Method for Sensorless Brushless DC (BLDC) Motor Drives," by Jianwen Shao, Virginia Polytechnic Institute and State University, Blacksburg, Va., September, 2003 (available at http://scholar.lib.vt.edu/theses/available/etd-09152003-171904/unrestricted/T.pdf).

In some implementations, the back EMF may also be monitored and used to detect faults in operation of the IOL injection device. For instance, due to the geometry of the intraocular lens and the volume of viscoelastic injected into the insertion cartridge, a properly loaded cartridge has a unique inherent viscous resistance to the plunger, and thus provides a known load on the motor. When compared to a loaded cartridge, the empty cartridge also has a distinct load signature. Because of the relationship between torque and speed in a DC motor, an increase in the load is reflected in a decrease in motor speed, for a given drive level. Conversely, a decrease in the load is reflected in an increase in motor speed. Because the back EMF of the motor is directly proportional to the motor's rotational speed, the level of the back EMF can be monitored to determine the motor's speed, and hence the applied load. By comparing the monitored back EMF level at a given instance to a predetermined threshold, the control processor 204 can detect whether or not the motor is operating at an expected speed. Thus, the control processor can detect faults in operation and automatically respond (e.g., by shutting down) and/or providing feedback to the user.

For example, a load cartridge containing less than the required viscoelastic in the cartridge will result in a back EMF higher than an expected level, in which case the control processor 204 can notify the user. Conversely, when the back EMF value is less than an expected level, it suggests an occluded cartridge. Again, the operation of the device can be shut down, and appropriate notice provided to the user. Of course, "normal" operation will fall within a range of back EMF levels. Thus, two separate thresholds may be used to detect excessive resistance to forward translation of the plunger and to detect insufficient resistance to translation of the plunger. (Distinct thresholds may apply to reverse translation of the plunger, in some embodiments.) The difference between these two thresholds defines the range of normal operation.

As discussed above, the magnitude of the back EMF level is directly proportional to the speed of the motor, and may be used to directly monitor the speed of the motor, and thus indirectly to monitor the load, i.e., the resistance to translation of the plunger. Alternatively, the speed of the motor may be monitored, using the back EMF, by counting zero crossings of the back EMF in a given time interval. This approach effectively counts rotations of the motor; because of the fixed relationship (defined by the gear box and the threads of the coupling mechanisms) between the motor and the linear translation, the number of motor rotations in a given time interval is directly proportional to the speed. This estimated speed may be compared, in the same manner as discussed above, to pre-determined thresholds to detect faults in operation.

In some implementations, counting positive-going and negative-going zero-crossing points of the back EMF provides an additional advantage, in that the longitudinal position of the plunger can be tracked at all times. Because the total number of net accumulated zero-crossing points is directly proportional to the linear translation of the plunger, the longitudinal position of the plunger within the device may be determined at any time, given only a calibrated reference point. This calibrated reference point may be defined at the time of manufacture, in some embodiments, or at the time of use in others. For example, a user may be instructed to fully retract the plunger and to then push a calibration button, setting a "zero" position for the plunger. Alternatively, a "hard stop" after retraction of the plunger can be automatically detected, using either of the methods discussed above, thus indicating the "zero" position of the plunger.

In those implementations that monitor the longitudinal position of the plunger, the tracked position information may be used along with the back EMF level at a given time to detect one or more fault conditions. For instance, the plunger will be engaged with the insertion cartridge only over a specific range of known lateral positions. Otherwise, e.g., as the tip of the plunger is approaching the cartridge, the plunger is expected to move with little resistance. The threshold or thresholds used to detect a fault may vary, depending on the lateral position of the plunger, to provide more accurate and/or more informative fault detection. For example, the threshold for detecting insufficient resistance to motion of the plunger may be set to a level corresponding to zero resistance for a range of lateral positions over which free movement of the plunger is expected. Over that same range, the threshold for detecting excessive resistance may be set to a level corresponding to a resistance level somewhat lower than is expected when the plunger begins to engage the insertion cartridge. For lateral positions in which the plunger is fully engaged with the cartridge, both thresholds may be adjusted to correspond to higher resistance levels.

Similarly, the threshold levels may vary with the direction of the plunger movement, and/or between two or more modes of operation. For example, a separate operational mode may be defined for installation of a removable plunger tip, in some implementations, as was described above. In this installation mode, the fault detection thresholds may be quite different than for the normal operating mode, to account for the expected resistance when the push rod of the plunger assembly engages the plunger tip and the expected backwards resistance when the plunger tip is extracted from the plunger tip wrench.

In some implementations, one or more of the above-discussed thresholds is pre-determined, e.g., by factory calibration, and stored in memory in or accessible to control processor 204. (Those skilled in the art will appreciate that this memory may comprise program memory or a separate memory storing factory-determined parameters or the like, and may include any of several conventional memory types, including ROM, PROM, EEPROM, flash, etc.) In some implementations, the thresholds used during operation may be adjusted relative to a "no-load" back EMF level or corresponding "no-load" rotational speed determined upon starting up the motor. As was briefly discussed, this may be facilitated by designing the drive system of the IOL injector so that it has a short interval upon each reversal in direction during which the drive system is not engaged with the plunger. One design approach is shown in FIG. 8B, and was discussed above. In such implementations, the "no-load" level for back EMF or speed may be measured and used to establish a baseline level. This baseline level may be used to scale and/or translate stored threshold levels to obtain more accurate operational thresholds.

Figure 26:
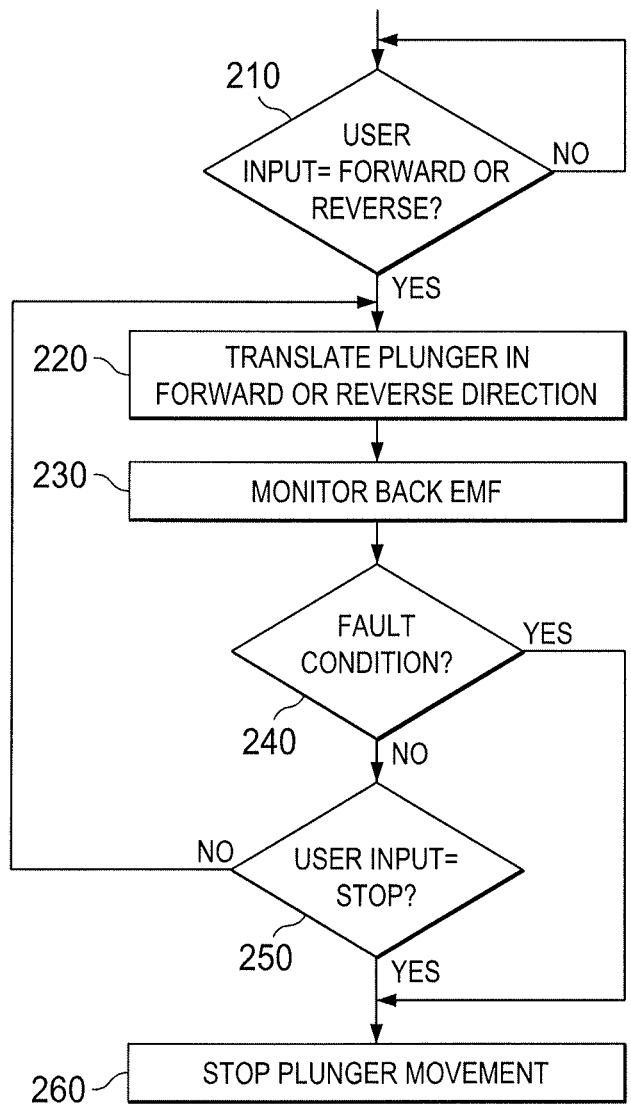
FIG. 26 is a process flow diagram of an example method for controlling an IOL injection device.

With the preceding discussions in mind, those skilled in the art will appreciate that the process flow diagram of FIG. 26 illustrates an exemplary implementation of a method for controlling an intraocular lens injection device according to any of the mechanical configurations discussed above and variations thereof. Those skilled in the art will appreciate that this particular process flow is not intending to be limiting; numerous variations of this method falling within the scope of the present disclosure will be apparent in view of the preceding discussion. Those skilled in the art will further appreciate that the processing flow of FIG. 26 may be implemented in software or firmware stored in program memory within or associated with control processor 204, for example, which memory may comprise one or more of various conventional types including read-only memory (ROM), programmable read-only memory (PROM), flash memory, magnetic or optical memory devices, or the like.

In any case, the process flow illustrated in FIG. 26 begins with IOL injection device in an inactive state. The device checks for user input indicating that actuation of the plunger assembly should begin, as shown at block 210. This user input may originate at any of a number of conventional user input devices, such as a keypad or touchscreen at an operator console connected by cable to the IOL injection device, a foot-operated switch electrically connected to the IOL injection device by cable or via a console, or one or more switches or buttons on the body of the IOL injection device itself. In any case, in response to user input indicating that the plunger assembly should be moved, a control circuit begins translation of the plunger in the indicated direction, as shown at block 220.

As the plunger is moved, the back EMF from the electric motor is monitored, as shown at block 230, according to any of the techniques discussed above. In some implementations, the magnitude of the back EMF level is monitored and compared to one or more pre-determined thresholds. In other implementations, zero-crossings of the back EMF are detected and counted for a pre-determined time interval, to get an indication of the plunger's speed, and compared to one or more pre-determined thresholds. If a fault condition is detected, as indicated at block 240, the movement of the plunger may be immediately suspended, as shown at block 260. As discussed above, the detected fault condition may correspond to excessive resistance to forward or backwards movement of the plunger, compared to pre-determined threshold levels, or insufficient resistance to forward or backwards movement of the plunger, compared to pre-determined threshold levels. In any of these cases, the threshold level for fault detection may vary according to a tracked longitudinal position of the plunger, as discussed earlier. Furthermore, the operational threshold levels may be adjusted according to a baseline resistance or operating speed determined during a "no-load" condition.

In some implementations, the stopping of the plunger's movement in response to a detected fault may be accompanied with or followed by an alert to the user, indicating the fault. In some cases, a message identifying a particular type of fault (e.g., "blocked cartridge", "empty cartridge", or the like) may be provided to the user via a graphical user interface on an operator's console. If a fault condition is not detected at block 240, then the status of the user input is checked, as shown at block 250. If the user input indicates that movement of the plunger should be stopped, then the motor is deactivated and the plunger's translation is stopped, as shown at block 260. Otherwise, translation of the plunger continues, as shown at block 220, and the preceding operations are repeated until either a fault occurs or the user input indicates that the plunger assembly's movement should be stopped.

In the above discussion of the process flow of FIG. 26, it was assumed that translation of the plunger continues, once initiated, until user input directs a stop or until a fault condition is detected. Those skilled in the art that the plunger motion may be limited at either or both ends by a mechanical stop. In some embodiments, these mechanical stops may be detected by the same fault detection mechanisms as described above, i.e., by monitoring the back EMF levels and/or the speed of the motor. Alternatively, some embodiments may prevent the plunger from reaching the mechanical stops by tracking the longitudinal position of the plunger, as described above, and automatically stopping the plunger's movement before it reaches a mechanical stop.

Figure 27:
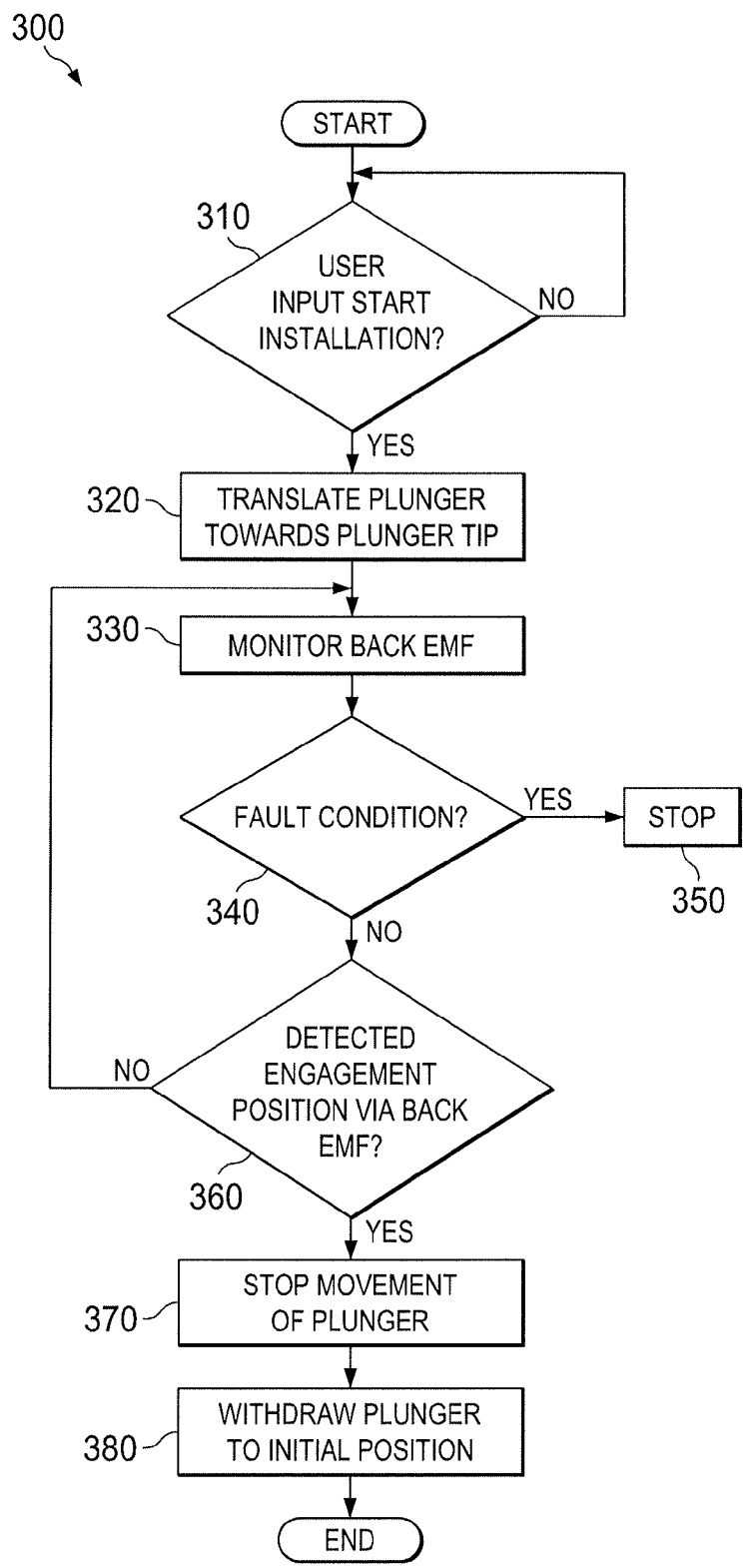
FIG. 27 is a process flow diagram of an example method for installing a plunger tip to a plunger of an example IOL injection device.

As mentioned above, utilization of the back EMF of the motor 42 may also be used to install the plunger tip, such as plunger tip 25, onto the plunger, such as plunger 32. FIG. 27 is an example flowchart illustrating an example method 300 for installing the plunger tip onto the plunger. At 310, a user provides an input to the IOL injector device, such as IOL injector device 10 or 158. The user input may be provided by any suitable input device, such as a keypad or touchscreen at an operator console connected by cable to the IOL injection device, a foot-operated switch coupled to the IOL injection device by cable or via a console, or one or more switches or buttons on the body of the IOL injection device itself. At 320, the plunger is translated towards to the plunger tip from an initial position (e.g., as shown in FIG. 29). The plunger tip may be provided in a plunger tip wrench, such as plunger tip wrench 90 or plunger tip wrench 100. As explained above, the plunger tip wrench is operable to align and secure the plunger tip relative to the IOL injector device. In some instances, the back EMF of the IOL injector device's motor may be monitored at 340 to detect the presence of a fault condition, as described above. If a fault condition is detected, movement of the plunger may be stopped and/or a warning indication may be provided to a user at 350. If no fault is detected, movement of the plunger is continued. The back EMF may be monitored throughout the installation procedure or at one or more times during the installation procedure.

At 360, at determination is made as to whether the position at which the plunger engages the plunger tip ("engagement position") is reached. The position of the plunger may be determined using one or more of the methods described above. For example, the position of the plunger may be determined by counting positive-going and/or negative-going zero-crossing points of the back EMF to determine the longitudinal position of the plunger. If the engagement position is not reached, monitoring of the back EMF at 330 continues until the engagement position is reached or, optionally, until a fault is detected. If the engagement position is detected, movement of the plunger is stopped at 370 (e.g., as shown in FIG. 30). At 380, the plunger and the coupled plunger tip are returned to the initial position.

Figure 31:
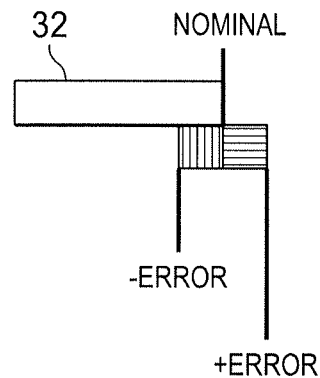
FIGS. 31-33 show an example plunger at a negative error position, a nominal position, and a positive error position, respectively, during the installation of a plunger tip.
Figure 32:
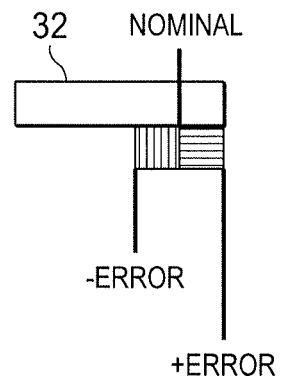
Figure 33:
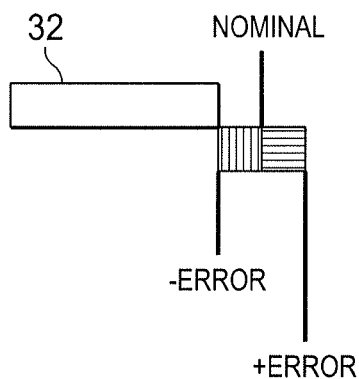

A certain amount of positional error may be associated with determining the longitudinal position of the plunger using back EMF. For example, for a designated position of the plunger, i.e., a position of the plunger along the longitudinal axis of the IOL injection device, there may be a positive positional error in which the actual position of the plunger is beyond the designated position ("positive error position") and a negative positional error in which the actual position of the plunger is short of the designated position ("negative error position"). FIGS. 31-33 show the position of the plunger 32 with respect to the designated position. In FIG. 31, the plunger 32 is at the nominal designated position. That is, the plunger 32 has obtained the designated position. FIG. 32 shows the plunger 32 at the positive error position, and FIG. 33 shows the plunger 32 at the negative error position.

Figure 34:
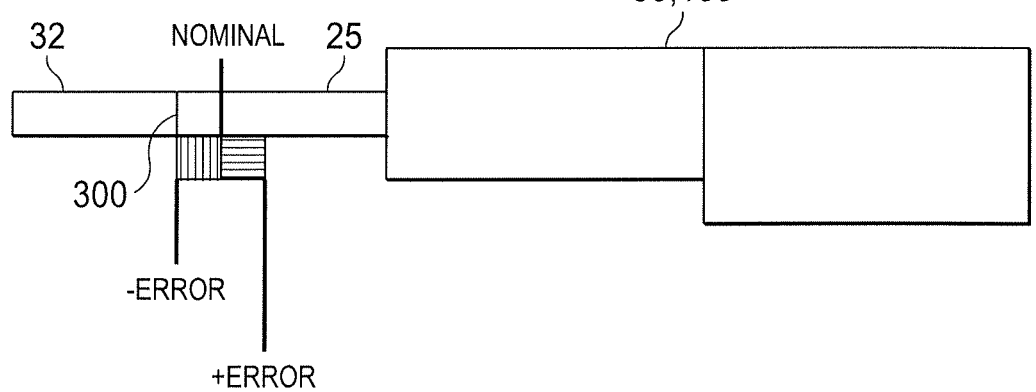
FIG. 34 is a schematic showing respective positions of a plunger tip wrench, a plunger tip, and a plunger during an example plunger tip installation procedure.

To ensure that the plunger tip is coupled to the plunger regardless as to what positional error may be experienced by the plunger during installation of the plunger tip, the plunger wrench may be positioned within the carriage mount, such as carriage mount 140, so that an end of the plunger tip is located such that it will be engaged by the plunger whether the plunger reaches the positive error position, the negative error position, or any position in between. FIG. 34 shows a schematic diagram showing the plunger tip wrench, such as plunger tip wrench 90 or 100, at a position relative to the IOL injector device such that the end 300 of the plunger tip 25 extends to the negative error position. Thus, no matter which position the plunger attains, e.g., the negative error position, positive error position, or any position therebetween, the plunger 32 will always engage the plunger tip to couple the two together. Where the plunger 32 extends to beyond the negative error position, to the positive error position, or any position in between, the plunger 32 may cause the plunger tip and plunger tip wrench 90, 100 to be displaced an amount in the direction of arrow 310.

For example, in some instances, when the end 300 of the plunger tip 25 is located at the negative error position and when where the plunger 32 extends therebeyond, the protrusions 136 of the plunger tip wrench 100 cooperate with the slot 148 in the cartridge mount 140 to provide resistance to the force applied by the plunger 32 to the plunger tip 25 while providing sufficient compliance to allow an amount of displacement of the plunger tip wrench 100 relative to the carriage mount 140 and while also maintaining proper orientation of the plunger tip 25 relative to the plunger 32.

Alternatively, in other implementations, the back EMF may reach a value when the plunger 32 engages the plunger tip 25 that indicates the engagement therebetween. The control circuit, such as control circuit 200, may be operable to detect this back EMF and determine that engagement has occurred. Thereafter, the IOL injector device may stop extension of the plunger and withdraw the plunger to the initial position.

It should be understood that, although many aspects have been described herein, some implementations may include all of the features, while others may include some features while omitting others. That is, various implementations may include one, some, or all of the features described herein. Further, a number of implementations have been described. Nevertheless, it will be understood that various modifications may be made without departing from the spirit and scope of the disclosure. Accordingly, other implementations are within the scope of the following claims.

What is claimed is:

1. A method of coupling a plunger tip to a plunger of an IOL injection device, the method comprising:

locating a plunger tip in alignment with the plunger;

extending the plunger from an initial position towards the plunger tip to an engagement position;

coupling the plunger and the plunger tip together; and retracting the plunger and plunger tip to the initial position, wherein extending the plunger from an initial position towards the plunger tip to an engagement position comprises actuating a motor of the IOL injection device to extend the plunger from the initial position to the engagement position, and the method further comprising:

detecting a position of the plunger utilizing a back electromotive force (EMF) of the motor, a position of the plunger detected by the back EMF being within a range of a negative error position corresponding to a negative positional error and a positive error position corresponding to a positive positional error.

2. The method of claim 1 further comprising:

releasably retaining the plunger tip within a plunger tip wrench, wherein locating a plunger tip in alignment with the plunger comprises coupling the plunger tip wrench to a mount of the IOL injection device such that the plunger tip is aligned and in a desired orientation relative to the plunger.

3. The method of claim 1, wherein locating a plunger tip in alignment with the plunger comprises locating an end of the plunger tip at a position corresponding to the negative positional error such that the plunger contacts the plunger tip within the entire range between the negative error position and the positive error position when the plunger is extended from the initial position to the engagement position.

4. The method of claim 3 further comprising monitoring the back EMF to detect a fault condition.

\* \* \* \* \*